US006660274B2

(12) United States Patent
Philipp

(10) Patent No.: US 6,660,274 B2
(45) Date of Patent: Dec. 9, 2003

(54) SURFACE ANTIGENS AND PROTEINS USEFUL IN COMPOSITIONS FOR THE DIAGNOSIS AND PREVENTION OF LYME DISEASE

(75) Inventor: Mario T. Philipp, Mandeville, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 25 days.

(21) Appl. No.: 09/445,803

(22) PCT Filed: Jun. 29, 1998

(86) PCT No.: PCT/US98/13551
§ 371 (c)(1),
(2), (4) Date: Dec. 13, 1999

(87) PCT Pub. No.: WO99/00413
PCT Pub. Date: Jan. 7, 1999

(65) Prior Publication Data
US 2003/0059894 A1 Mar. 27, 2003

Related U.S. Application Data

(60) Provisional application No. 60/051,271, filed on Jun. 30, 1997.

(51) Int. Cl.[7] .................. A61K 39/02; A61K 49/00; C12Q 3/00; G01N 33/554

(52) U.S. Cl. .................. 424/234.1; 424/9.1; 424/9.2; 424/139.1; 424/164.1; 424/184.1; 424/185.1; 424/190.1; 424/192.1; 424/200.1; 435/4; 435/7.1; 435/7.2; 435/7.32; 435/320.1; 435/440; 435/471; 436/501; 530/300; 530/350

(58) Field of Search .................. 424/9.1, 9.2, 139.1, 424/164.1, 184.1, 185.1, 190.1, 192.1, 200.1, 234.1; 435/4, 7.1, 7.2, 7.32, 440, 471, 320.1; 436/501; 530/300, 750; 536/23.1, 23.7

(56) References Cited

U.S. PATENT DOCUMENTS

485,551 A    11/1892  Luscombe
6,437,116 B1  8/2002  Norris et al.

FOREIGN PATENT DOCUMENTS

| EP | 339695 | 11/1989 |
| EP | 465204 | 1/1992 |
| WO | WO 90/04411 | 5/1990 |
| WO | WO 91/09870 | 7/1991 |
| WO | WO 91/13630 | 9/1991 |
| WO | WO 92/00055 | 1/1992 |

OTHER PUBLICATIONS

Zhang, J.–R., et al "Antigenic variation in Lyme Disease Borreliae by promiscuous recombination of VMP–like sequence cassettes", Cell, vol. 89, pp. 275–285, Apr., 1997.*

E. Fikrig et al., "*Borrelia burgdorferi* P35 and P37 Proteins, Expressed In Vivo, Elicit Protective Immunity," *Immunity*, 6:531–539 (May 1997).

A. Aberer, et al., "Molecular Mimicry and Lyme Borreliosis: A Shared Antigenic Determinant Between *Borrelia burgdorferi* and Human Tissue," *Ann. Neurol.*, 26:732–737 (Dec. 1989).

G.S. Gassmann et al., "N–Terminal Amino Acid Sequence of the *Borrelia burgdorferi* flagellin," *FEMS Microbiol. Lett.*, 60:101–106 (Jul. 1, 1989).

J.R. Zhang et al., "Antigenic Variation in Lyme Disease Borreliae by Promiscuous Recombination of VMP–like Sequence Cassettes," *Cell*, 89(2):275–285 (Apr. 18, 1997).

R. Ramamoorthy, "Molecular Characterization, Genomic Arrangement, and Expression of bmpD, a New Member of the bmp Class of Genes Encoding Membrane Proteins of *Borrelia burgdorferi*," *Infect. Immun.*, 64(4):1259–1264 (Apr. 1996).

J.R. Zhang et al., "Kinetics and in vivo Induction of vlsE Antigenic Variation in *Borrelia burgdorferi*," EMBL/GenBank/DDBJ databases, Accession No. AF034515, Jun. 2, 1998.

H. Kawabata et al., "Genetic and Immunological Analyses of Vls (VMP–like Sequences) if *Borrelia burgdorferi*," EMBL/GenBank/DDBJ databases, Accession No. AB011063, Mar. 13, 1998.

J.R. Zhang et al., "Kinetics and in vivo Induction of vlsE Antigenic Variation in *Borrelia burgdorferi*," EMBL/GenBank/DDBJ databases, Accession No. AF034525, Jun. 2, 1998.

J.R. Zhang et al., "Kinetics and In Vivo Induction of Genetic Variation of vlsE in *Borrelia burgdorferi*," EMBL/GenBank/DDBJ Databases, Accession No., AF034523, Jun. 2, 1998.

A.G. Barbour et al., "Variation in a Major Surface Protein of Lyme Disease Spirochete," *Infect. Immun.*, 45:94–100 (Jul. 1984).

W.J. Simpson et al., "Reactivity of Human Lyme Borreliosis Sera with a 39–Kilodalton Antigen Specific to *Borrelia burgdorferi*," *J. Clin. Microbiol.*, 28:1329–1337 (Jun. 1990).

(List continued on next page.)

Primary Examiner—Rodney P Swartz
(74) Attorney, Agent, or Firm—Howson and Howson

(57) ABSTRACT

A novel isolated *Borrielia burgdorferi* sensu lato surface antigen is characterized by a relative molecular mass of 39.5 kDa. This antigen is expressed in vitro by spirochetes of a *B. burgdorferi* sensu lato strain. This antigen induces antibodies which kill spirochetes of a *B. burgdorferi* sensu lato strain by ADCK in vitro. Novel Borrelia cassette string protein or fragments thereof are also useful, as is the P39.5 protein in diagnosing Lyme disease and in compositions for treatment or prophylaxis thereof.

6 Claims, 6 Drawing Sheets

OTHER PUBLICATIONS

K. Hansen et al., "Immunochemical Characterization of and Isolation of the Gene for a *Borrelia burgdorferi* Immunodominant 60–Kilodalton Antigen Common to a Wider Range of Bacteria," *Infect. Immun.*, 56:2047–2053 (Aug. 1988).

K. Hansen et al., "Measurement of Antibodies to the *Borrelia burgdorferi* Flagellum Improves Serodiagnosis in Lyme disease," *J. Clin. Microbiol.*, 26:338–346 (Feb. 1988).

B. Wilske et al., "Immunochemical and Immunological Analysis of European *Borrelia burgdorferi* Strains," *Zbl. Bakt. Hyg. A.*, 263:92–102 (Dec. 1986).

D.W. Dorward et al., "Immune Capture and Detection of *Borrelia burgdorferi* Antigens in Urine, Blood, or Tissues from Infected Ticks, Mice, Dogs, and Humans," *J. Clin. Microbiol.*, 29:1162–1170 (Jun. 1991).

L. Bakken et al., "Interlaboratory Comparison of Test Results for Detection of Lyme Disease by 516 Participants in the Wisconsin State Laboratory of Hygiene/College of American Pathologist Proficiency Testing Program," *J. Clin. Microbiol.*, 35:537 (Mar. 1997).

J.G. Donahue et al., "Reservoir Competence of White–Footed Mice for Lyme Disease Spirochetes," *Am. J. Trop. Med. Hyg.*, 36:92–96 (Jan. 1987).

R. T. Green et al., "Immunoblot Analysis of Immunoglobulin G Response to the Lyme Disease Agent (*Borrelia burgdorferi*) in Experimentally and Naturally Exposed Dogs," *J. Clin. Micro.*, 26:648–653 (Apr. 1988).

D. L. Cox et al., "Limited Surface Exposure of *Borrelia burgdorferi* Outer Surface Lipoproteins," *Proc. Natl. Acad. Sci. USA*, 93:7973–7978 (Jul. 1996).

M. Kay et al., "In vivo Hepatic Gene Therapy: Complete Albeit Transient Correction of Factor IX Deficiency in Hemophilia B Dogs," *Proc. Natl. Acad. Sci. USA*, 91:2353 (Mar. 1994).

S. Ishibashi et al., "Hypercholesterolemia in Low Density Lipoprotein Receptor Knockout Mice and its Reversal by Adenovirus–Mediated Gene Delivery," *J. Clin. Invest.*, 92:883 (Aug. 1993).

J.R. Zhang et al., "Kinetics and In Vivo Induction of Genetic Variation of vlse in *Borrelia burgdorferi*," *Infect. Immun.*, 66(8):3689–3697 (Aug. 1998).

J. R. Zhang et al., "Genetic Variation of the *Borrelia burgdorferi* Gene vlsE Involves Cassette–Specific, Segmental Gene Conversion," *Infect. Immun.*, 66:3698–3704 (Aug. 1998).

S. M. Kochi et al., "Facilitation of Complement–Dependent Killing of the Lyme Disease Spirochete, *Borrelia burgdorferi*, by Specific Immunoglobulin G Fab Antibody Fragments," *Infect. Immun.*, 61:2532–2536 (Jun. 1993).

D.M. Reinitz et al., "Variable and Conserved Structural Elements of Trypanosome Variant Surface Glycoproteins," *Mol. Biochem. Parasitol.*, 51:119–132 (Feb. 1992).

P. Marrack and J. Kappler, "Subversion of the Immune System by Pathogens," *Cell*, 76:323–332 (Jan. 28, 1994).

R. R. Garrity et al., "Refocusing Neutralizing Antibody Response by Targeted Dampening of an Immunodominant Epitope," *J. Immunol.*, 159:279–289 (Jul. 1, 1997).

Lightfoot et al., "Empiric Parenteral Antibiotic Treatment of Patients with Fibromyalgia and Fatigue and a Positive Serlogic Result for Lyme Disease," *Ann. Intern Med.*, 129:503–509 (Sep. 15, 1993).

Tugwell et al., "Laboratory Evaluation in the Diagnosis of Lyme Disease," *Ann. Intern. Med.*, 127:1109–1123 (Dec. 15, 1997).

K.T. Forest et al., "Assembly and Antigenicity of the *Neisseria gonorrhoeae* Pilus Mapped with Antibodies," *Infect. Immun.*, 64:644–652 (Feb. 1996).

H. Kawabata et al., "Genetic and Immunological Analyses of Vls (VMP–like sequences) of *Borrelia burgdorferi,*" *Microb. Pathog.*, 24:155–166 (Mar. 1998).

M. Philipp et al., "Safety and Immunogenicity of Recombinant Outer Surface Protein A (OspA)Vaccine Formulations in the Rhesus Monkey," *J. Spirochetal and Tick–borne Disease*, 3:67–79 (Mar. 1996).

A. DeSilva et al., "*Borrelia burgdorferi* OspA is an Arthropod–specific Transmission–blocking Lyme Disease Vaccine," *J. Exp. Med.*, 183:271–275 (Jan. 1996).

T. Mather et al., "*Ixodes* Saliva: Vector Competence for *Borrelia burgdorferi* and Potential Vaccine Strategies", in VII International Congress on Lyme Borreliosis, San Francisco, CA 1996.

A. Sadziene et al., "Antibody–resistant Mutants of *Borrelia burgdorferi*: In Vitro Selection and Characterization," *J. Exp. Med.*, 176:799–809 (Sep. 1992).

A. DeSilva et al., "Growth and Migration of *Borrelia burgdorferi* in Ixodes Ticks During Blood Feeding," *Am. J. Trop. Med.*, 53:397–404 (Oct. 1995).

P. Rosa et al., "Recombination between Genes Encoding Major Outer Surface Proteins A and B of *Borrelia burgdorferi,*" *Mol. Microbial.* 6:3031–3040 (1992).

T. Schwan et al., "Distribution and Molecular Analysis of Lyme Disease Spirochetes, *Borrelia burgdorferi*, Isolated from Ticks throughout California," *J. Clin. Microbiol.*, 31:3096–3108 (Dec. 1993).

F.T. Liang et al., "Sensitive and Specific Serodiagnosis of Lyme Disease by Enzyme–Linked Immunosorbent Assay with a Peptide Based on an Immunodominant Conserved Region of *Borrelia burgdorferi* VlsE," *J. Clin. Microbiol.*, 37(12): 3990–996 (Dec. 1999).

F.T. Liang and M.T. Philipp, "Analysis of Antibody Response to Invariable Regions of VlsE, the Variable Surface Antigen of *Borrelia burgdorferi,*" *Infect. Immun.*, 67(12):6702–6706 (Dec. 1999).

F.T. Liang et al., "An Immunodominant Conserved Region Within the Variable Domain of VlsE, the Variable Surface Antigen of *Borrelia burgdorferi,*" *J. Immunol.*, 163(10):5566–5573 (Nov. 15, 1999).

* cited by examiner

| Blocks | %Identity |
|---|---|
| IA vs. IB | 70% |
| IIA vs. IIB | 91% |
| A vs. B | 84% |
| B vs. C | 90% |

SURFACE ANTIGENS AND PROTEINS USEFUL IN COMPOSITIONS FOR THE DIAGNOSIS AND PREVENTION OF LYME DISEASE

CROSS-REFERENCE TO RELATED APPLICATIONS

This is a 371 of PCT/US98/13551, filed Jun. 29, 1998, which claims the benefit of the priority of U. S. patent application Ser. No. 60/051,271, filed June 30, 1997.

This invention was funded in part by the National Institutes of Health Grant Nos. ROI AI35027 and RR/AE00164-32. The United States government has certain rights in this invention.

FIELD OF THE INVENTION

The present invention relates generally to the field of pharmaceutical and diagnostic compositions useful in the diagnosis, treatment and prophylaxis of Lyme borreliosis. More specifically, the invention provides an isolated natural surface antigen of Borellia and antibodies thereto for use in the diagnosis, treatment or prevention of Lyme disease.

BACKGROUND OF THE INVENTION

*Borrelia burgdorferi* (sensu lato) is a generic term which encompasses several Borrelia species associated with, and believed to be, the causative agent of Lyme borreliosis (Lyme disease): *B. burgdorferi* sensu stricto, *B. garinii*, and *B. afzelii*. This disease is transmitted by the bite of various species of Ixodes ticks carrying the spirochete. The main reservoir of the infection in the United States is the white footed mouse, *Peromyscus leucopus*, and the infection can be transmitted to many mammalian species including dogs, cats, and man [J. G. Donahue, et al, *Am. J. Trop. Med. Hyg.*, 36:92–96 (1987); R. T. Green, et al, *J. Clin. Micro.*, 26:648–653 (1988)]. Despite the presence of an active immune response, the disease persists for years in patients. Such persistence is postulated to be the result, at least in part, of antigenic variation in the bacterial proteins [J. R. Zhang et al, *Cell*, 89:275–285 (1997)].

The diagnosis of Lyme disease in humans and animals has been compromised by the lack of definitive serology leading to rapid and accurate testing. Current diagnostic tests suffer from low sensitivity and specificity, as illustrated by a recent survey of diagnostic laboratories' performance issued by the Wisconsin State Laboratory of Hygiene [L. Bakken et al, *J. Clin. Microbiol.*, 35:537 (1997)]. A simple, sensitive and specific diagnostic composition and method for early detection of Lyme disease is needed in the art.

Publications relating to proteins and polypeptides of *Borrelia burgdorferi* have suggested their use as diagnostic or pharmaceutical agents. Such proteins and polypeptides include outer surface proteins A and B (OspA and OspB), flagellin, and other proteins designated P21, P39, P66, and P83 according to their estimated molecular weights [A. G. Barbour et al, *Infect. Immun* 45:94–100 (1984); W. J. Simpson et al, *J. Clin. Microbiol.*, 28 1329–1337 (1990); K. Hansen et al, *Infect Immun.*, 56:2047–2053 (1988); K. Hansen et al, *Infect. J. Clin. Microbiol.*, 26 338–346 (1988); B. Wilske et al, *Zentral, Bakteriol. Parasitenkd. Infektionshkr. Hyg. Abt.* 1 Orig. Reihe. A. 263:92–102 (1986); D. W. Dorward et al, *J. Clin. Microbiol.*, 29:1162–1170(1991); published NTIS U.S. patent application No. 485,551; European patent application No. 465,204, published Jan. 8, 1992; International Patent Application No. PCT/US91/01500, published Sep. 19, 1991; International Patent Application No. PCT/EP90/02282, published Jul. 11, 1991; International Patent Application No. PCT/DK89/00248, published May 3, 1990; International patent application No. WO92/00055, published Jan. 9, 1992].

A preferred protein candidate for a vaccine is OspA [M. Philipp et al, *J. Spirochetal and Tick-borne Diseases*, 3:67–79 (1996)]. The expression of OspA is either abrogated or down-regulated when the spirochetes are en route from the tick's midgut to the salivary glands, as blood feeding is taking place [A. DeSilva et al, *J Exp. Med.* 183:271–275 (1996)]. This phenomenon generates potential problems that may diminish the OspA vaccine's efficacy. Spirochetal attrition may occur only within the tick midgut [A. DeSilva et al, cited above] and not upon infection of the vertebrate host. Because the saliva of *Ixodes scapularis* contains a decomplementing factor [T. Mather et al, "Ixodes saliva: vector competence for *Borrelia burgdorferi* and potential vaccine strategies", in VII International Congress on Lyme Borreliosis, San Francisco, Calif. (1996)], spirochetal attrition within the tick's midgut might occur via a mechanism involving only antibody and not complement.

Although the mode of action of antibody-dependent killing is not fully understood, it appears to be a less efficient mechanism of killing than that mediated by antibody and complement, acting together [M. Sole et al, *Infect. Immunol.*, 66:2540–2546 (1998)]. Thus, it may permit evasion from the midgut of those spirochetes that have a low surface density of OspA. Indeed, although OspA is an abundant *B. burgdorferi* protein, only a minor fraction of OspA molecules is exposed on the outer surface of the spirochete [D. Cox et al, *Proc. Natl. Acad. Sci.*, 93:7973–7978 (1996)]. Thus, small variations in the absolute number of OspA surface molecules may cause significant differences in the spirochete attrition rate and make it possible for a fraction of the resident spirochetes to abscond to the salivary glands.

OspA escape mutants will readily avoid killing altogether, and if they are infectious to the vertebrate host, they will contribute to diminish the OspA vaccine efficacy even further. In clonal populations of *B. burgdorferi* which are allowed to grow in vitro, the prevalence of mutants that resist killing by anti-OspA antibody ranges between $10^{-5}$ and $10^{-2}$ [A. Sadziene et al, *J. Exp. Med*, 176:799–809 (1992)]. If such frequencies are reproduced in a feeding nymph, in which spirochete numbers may reach a mean of 7,848 within 15 hours of attachment [A. DeSilva et al, *Am. J. Trop. Med. Hyg.*, 53:397–404 (1995)] then several mutants may be present in a single tick. Typical mutant phenotypes include those that express neither OspA nor OspB and, frequently, expressors of a chimeric molecule composed of an N-terminal fragment of OspA fused to a C-terminal fragment of OspB. These deletion mutants have been found in multiple strains of *B. burgdorferi* [P. Rosa et al, *Mol. Microbiol.*, 6:3031–3040 (1992)] and in several tick isolates from California [T. Schwan et al, *J. Clin. Microbiol.*, 31:3096–3108 (1993)]. Chimeric (deletion) mutants, which are able to resist killing with anti-OspA antibody alone, are killed by the combined action of antibody and complement. Since complement appears to be nonfunctional within the tick [T. Mather et al, cited above], and OspA, and probably its chimeric form as well, are not expressed within the vertebrate host shortly after infection, chimeric OspA escape mutants could infect the vertebrate host. Further, it is estimated that up to 2% of Ixodid ticks are only partially fed and are therefore still questing [Y. Lobet, personal communication]. If such ticks have taken their incomplete meal from a *B. burgdorferi*-infected host, they will have spirochetes in their salivary glands which do not express OspA and which will readily infect an OspA-vaccinated host.

No booster effect has been observed [M. Philipp et al, cited above] nor should one be expected upon spirochetal challenge of an OspA-vaccinated host. Hence, the OspA vaccine may require repeated administrations to maintain effective antibody titers.

There is a thus a need in the art for additional, and improved, methods and compositions for prevention of Lyme disease in humans and animals, and for treatment thereof.

SUMMARY OF THE INVENTION

The present invention satisfies the need in the art by providing methods and compositions for prevention of Lyme Disease based on spirochetal antigens that are expressed by the spirochete during its residence in the vertebrate host. Such methods and compositions may also be employed for the treatment of Lyme Disease.

In one aspect, the invention provides an isolated *Borrelia burgdorferi* sensu lato surface antigen which is expressed in vivo by the spirochete in the vertebrate host. The antigen, referred to herein as P39.5, is further characterized as having a relative molecular mass of 39.5 kDa. Fragments of this antigen are also useful in the compositions and methods of this invention.

In another aspect, the invention provides novel Borrelia cassette string polypeptides/proteins.

In yet another aspect, the invention provides nucleic acid sequences encoding P39.5 or a fragment thereof, such as P7-1, as well as nucleic acid sequences encoding other Borrelia cassette string proteins or fragments thereof. These nucleic acid sequences include sequences which hybridizes to the above sequences under stringent conditions, allelic variants thereof and deletion mutants thereof.

In another aspect, the invention provides novel proteins comprising fragments of the P39.5 protein sequence or cassette string protein sequences described above, optionally fused to, or mixed with, a second selected polypeptide or protein, which may be a protein of up to about 90% identity in its amino acid sequence with that of P39.5, or other Borrelia antigens, such as OspA, and proteins or polypeptides derived from other microorganisms.

In still another aspect, the invention provides novel protein compositions comprising the protein sequences of the antigen(s) described above, or fragments thereof, optionally mixed with a second selected polypeptide or protein, which may be a protein of up to about 90% identity in its amino acid sequence with that of P39.5, or other Borrelia antigens, such as OspA, and proteins or polypeptides derived from other microorganisms.

In still a further aspect, the invention provides a method for recombinantly producing the above-described P39.5 protein, fragments thereof or fusion proteins containing such fragments, by expressing a DNA sequence encoding the protein, fragment or fusion protein in a selected host cell, and isolating the protein therefrom. Host cells transformed with such DNA sequences are also provided herein.

In still another aspect, the invention provides an isolated antibody directed against the above-described P39.5 antigen, fragments thereof, cassette string proteins or fragments, or a fusion protein containing such fragments. These antibodies may be polyclonal. The present invention also provides a method for producing such antibodies comprising immunizing a human or an animal with an isolated antigen as described above, or with one or a mixture of more than one fragment(s) thereof, or fusion protein containing one or more fragment(s) of this invention. Other types of antibodies may be prepared from such immunized animals, e.g., recombinant, monoclonal, chimeric, humanized, etc.

In another aspect, the invention provides a therapeutic composition and methods for treating humans and/or animals with Lyme disease. The therapeutic composition contains an antibody, or protein, or fragment as described above and a suitable pharmaceutical carrier.

In a further aspect, the invention provides vaccine compositions and methods of vaccinating a human or animal patient against Lyme Disease by use of these above-described compositions. The compositions contain an effective amount of at least one Borrelia antigen of this invention, e.g., an antigen that is expressed in vitro by Borrelia spirochetes, said antigen having a relative molecular mass of 39,500 daltons, or antigenic fragment(s) thereof, or a fusion protein containing such a fragment, or cassette string protein(s), and a pharmaceutically acceptable carrier. The vaccine composition may contain the P39.5 protein, fragments thereof, fusion proteins or mixtures of proteins as described above.

In yet a further aspect, the invention provides vaccine compositions and methods of vaccinating a human or animal patient against Lyme Disease by use of nucleic acid compositions, e.g., DNA vaccines. The compositions contain an effective amount of a DNA sequence encoding at least one Borrelia antigen of this invention or antigenic fragment(s) thereof, cassette string antigen(s), or a fusion protein containing such a fragment, and an optional pharmaceutically acceptable carrier.

In yet a further aspect, the invention provides a method for diagnosing Lyme borreliosis in a human or animal. This method includes the steps of incubating an antigen or antibody of this invention, preferably conventionally labeled for detection, with a sample of biological fluids from a human or an animal to be diagnosed. In the presence of *B. burgdorferi* infection of the human or animal patient, an antigen-antibody complex is formed. Subsequently the reaction mixture is analyzed to determine the presence or absence of these antigen-antibody complexes. In a further embodiment, the diagnostic assay employs DNA sequences, preferably anti-sense sequences, sense sequences, of the antigen or fragments thereof, and diagnoses infection by the presence of sequences in a biological fluid from the patient that hybridizes thereto. Other conventional assay formats may be employed using reagents identified by this invention.

In another aspect the invention provides a kit for diagnosing infection with *B. burgdorferi* in a human or an animal patient sample which contains at least one antibody capable of binding at least one antigen of this invention of antigenic fragment(s) thereof, or a DNA sequence encoding one or more antigen(s) of this invention or an anti-sense sequence thereof. The antibodies and sequences may be optionally labeled for detection, or a detection system may be included in the kit.

Other aspects and advantages of the present invention are described further in the following detailed description of the preferred embodiments thereof.

Figure 2:
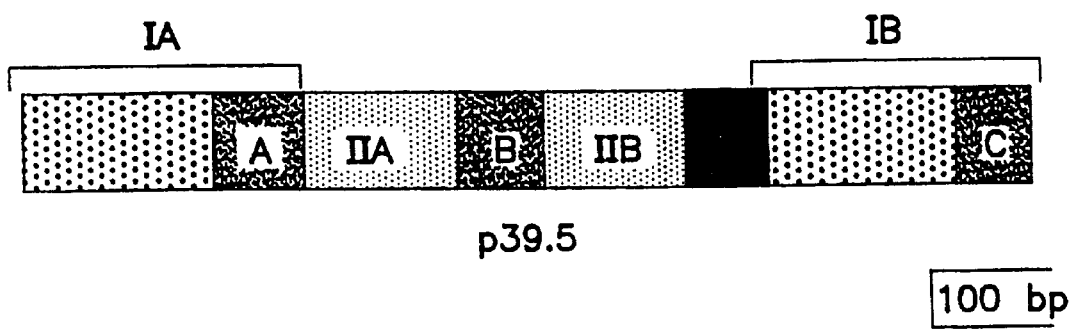

FIG. 2 is a schematic depiction of portions of the DNA sequence of the novel P39.5 encoding a single open reading frame which encodes a deduced protein of 37.7 kDa. This DNA fragment is named 7-1, and the deduced protein referred to as P7-1. The region in black is a unique region spanning about bp769 to about bp854 of SEQ ID NO: 1. The region labeled IA spans about bp 1 to about bp 309 of SEQ ID NO: 1; IB spans about bp 855 to about bp 1189 of SEQ ID NO: 1. Regions IA and IB have a 70% identity. Regions IIA, which spans about bp 310 to about bp494 of SEQ ID NO: 1 and IIB, which spans about bp 595 to about bp 769 of SEQ ID NO: 1, have a 91% identity. Regions A, which spans about bp 208 to about bp 309 of SEQ ID NO: 1, and B, which spans about bp 495 to about bp 595 of SEQ ID NO: 1, have an 84% identity. Regions B and C, which together span about bp 1090 to about bp 1189 of SEQ ID NO: 1, have a 90% identity.

Figure 3:
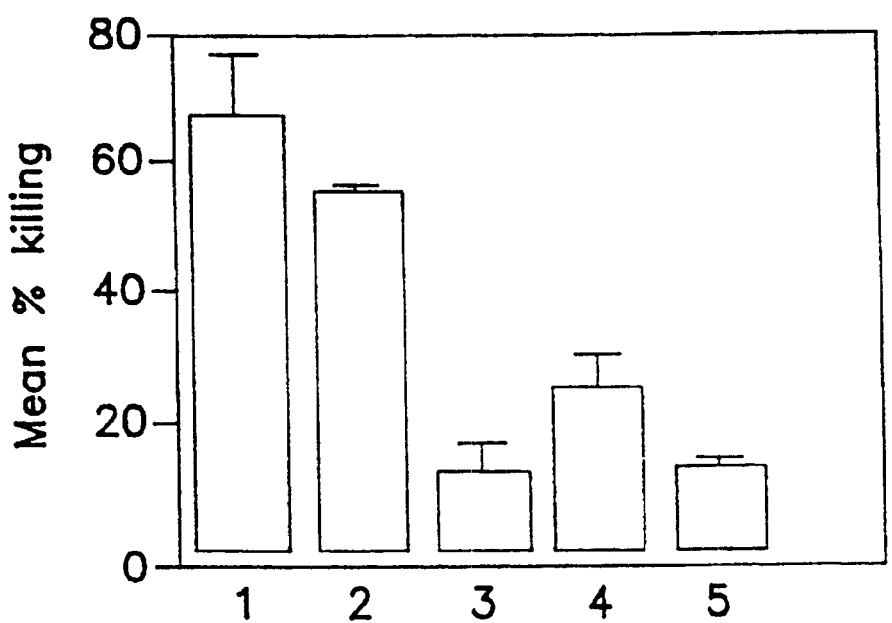

FIG. 3 is a bar graph which illustrates in vitro killing of IP90 spirochetes with: plasma of a monkey infected with JD1 spirochetes and monkey complement (bar 1); antibody from the same plasma which is affinity purified on native P39.5 and monkey complement (bar 2); the same antibody as described for bar 2 without complement (bar 3); complement alone (bar 4); and BSK-H medium alone (bar 5). Error bars represent the standard deviation of the mean of two determinations.

Figure 4:
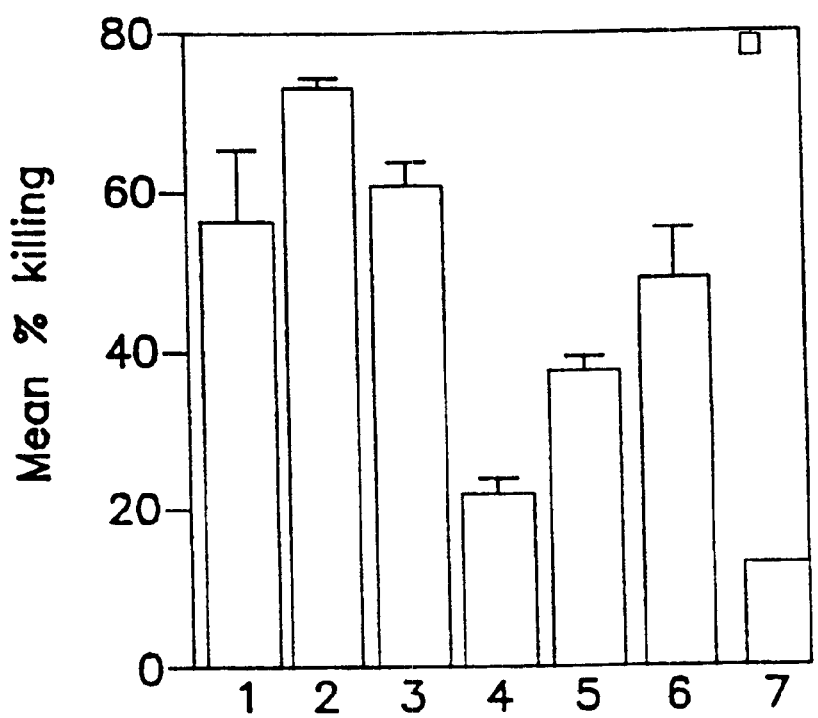

FIG. 4 is a bar graph showing ADCK of spirochetes of the IP90 strain using: a plasma pool from monkeys infected with *B. burgdorferi* JD1 at a dilution of 1:10 (bars 1, 5); pooled serum from mice immunized with a recombinant form of P7-1 (rP7-1) and Ribi adjuvant at 1:10 (bars 2,6); and 1:50 (bar 3); and mice immunized with Ribi adjuvant alone (bars 4,7). Monkey complement was used in ADCK of bars 1–4 and guinea pig complement in ADCK of bars 5–7. Error bars represent the standard error of the mean of two determinations.

Figure 5:
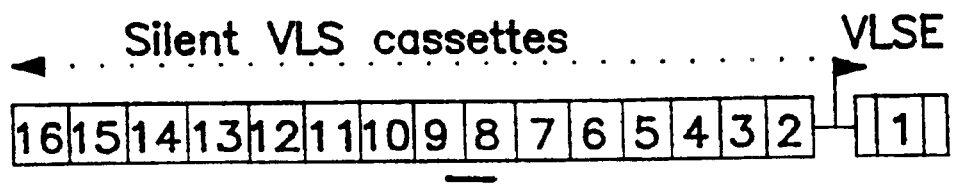

FIG. 5 is an illustration of the 'string' of silent VLS cassettes in a stretch of DNA about 8 kb in length, duplicated from J. R. Zhang et al, *Cell,* 89:275–285 (1997).

Figure 6:
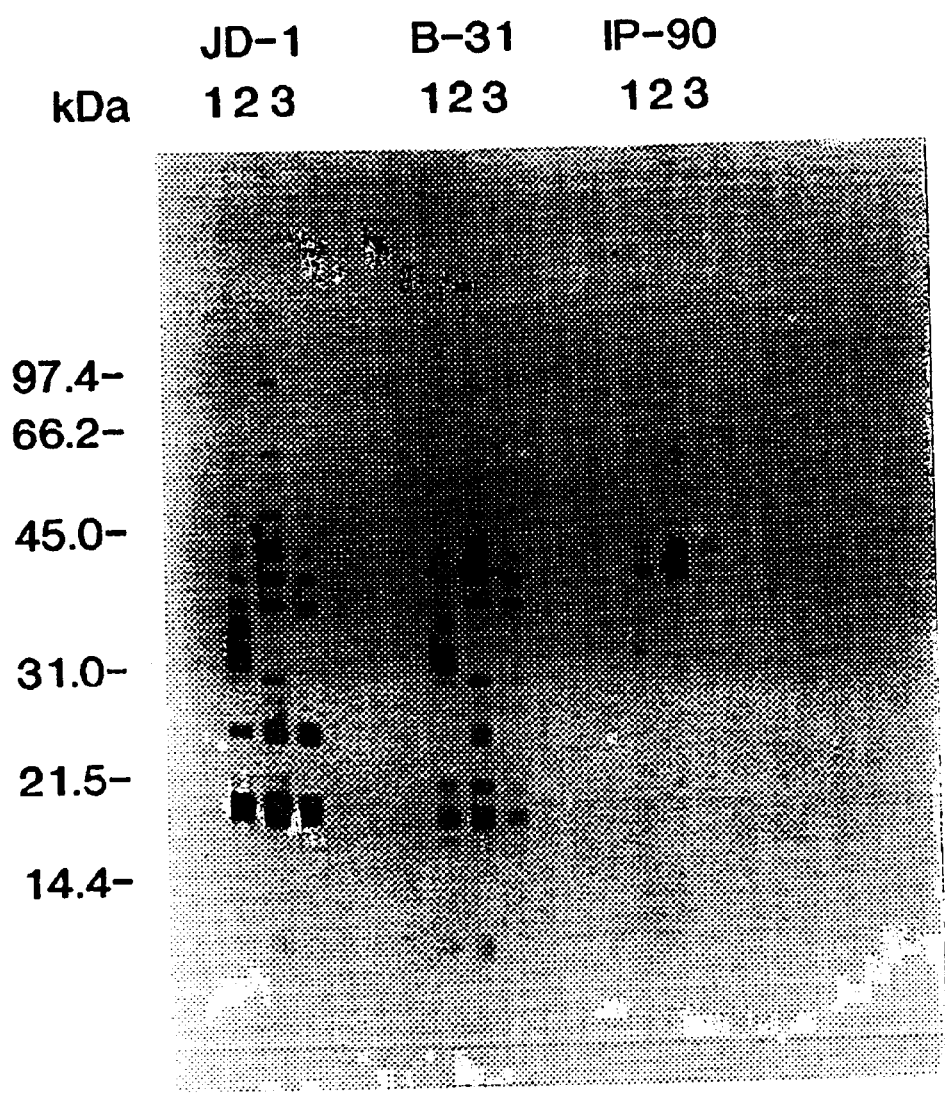

FIG. 6 is a Western blot of lysates from spirochetes of *B. burgdorferi* strains JD1 and B31, and *B. garinii* strain IP90 developed with serum from monkeys needle-inoculated (lanes 1) and tick-inoculated (lanes 2) with the JD1 spirochetes, and antibodies from the latter serum affinity purified off of whole live JD1 spirochetes (lanes 3).

Sequence Listings Designations

SEQ ID NO:1 is the nucleic acid sequence of clone 7-1.

SEQ ID NO:2 is the deduced protein sequence of clone 7-1.

SEQ ID NO:3 is the 5' end of the nucleic acid sequence of clone 1-1.

SEQ ID NO:4 is a partial nucleic acid sequence of clone 1-1, found in the middle of the nucleic acid sequence.

SEQ ID NO:5 is the 3' end of the nucleic acid sequence of clone 1-1.

SEQ ID NO:6 is the 5' end of the nucleic acid sequence of clone 3-1.

SEQ ID NO:7 is the 3' end of the nucleic acid sequence of clone 3-1.

SEQ ID NO:8 is the 5' end of the nucleic acid sequence of clone 6-1.

SEQ ID NO:9 is the 3' end of the nucleic acid sequence of clone 6-1.

SEQ ID NO:10 is the 5' end of the nucleic acid sequence of clone 9-1.

SEQ ID NO:11 is the 5' end of the nucleic acid sequence of clone 12-1.

SEQ ID NO:12 is the 3' end of the nucleic acid sequence of clone 12-1.

SEQ ID NO: 13 is a partial nucleic acid sequence obtained from clone 14 which, when added to the 5' terminus of clone 7-1 [SEQ ID NO: 1], forms a larger fragment of P39.5, i.e., P7-1. The first 5' terminal six bases are from the plasmid vector.

SEQ ID NO: 14 is the deduced protein sequence of SEQ ID NO: 13.

DETAILED DESCRIPTION OF THE INVENTION

The present invention provides a novel Borrelia surface antigen, P39.5, that is expressed by the spirochete when it resides in the vertebrate host ("in vivo"). This antigen is targeted by antibody-dependent, complement-mediated (ADCK) killing in vitro. This novel antigen, fragments thereof, antibodies developed thereto, the nucleic acid sequences encoding same, and the use of such antigens, antibodies and nucleic acid sequences in diagnostic, therapeutic and prophylactic compositions and methods for the treatment or prevention of Lyme Disease provide advantages over the use of other Borrelia proteins and antibodies in known compositions and methods for this purpose.

I. The P39.5 Antigen of the Invention

In one embodiment, the present invention provides a novel isolated Borrelia antigen, referred to as P39.5. This antigen is expressed both in vitro and in vivo by Borrelia spirochetes, e.g., spirochetes of *B. garinii* strain IP90. This antigen, or a homolog thereof, is also expressed in vivo by spirochetes of the *B. burgdorferi* sensu stricto strains JD1, B31 and NT1. This antigen has an apparent molecular mass of 39.5 kDa in IP90 spirochetes, and is functionally characterized by the ability to elicit antibody in animals during the course of a natural infection with Borrelia spirochetes. These induced antibodies kill IP90 spirochetes by ADCK in vitro. The elicited antibody also kills spirochetes of the $NT_1$ strain of *B. burgdorferi* sensu lato, a strain isolated from the cerebrospinal fluid of a patient in the United States, but not further characterized within the sensu lato complex of species. This strain was provided by Dr. Patricia Coyle, State University of New York at Stony Brook, N.Y.

The gene fragment, designated 7-1, from *Borrelia garinii* strain IP90 inserted in pBluescript II plasmid was transformed in *E. coli* and deposited with the American Type Culture Collection, 10801 University Boulevard, Manassas, Va. ("ATCC") on Jun. 27, 1997 under Accession No. 98478. When this gene fragment is expressed in *E. coli,* isolated as a pure protein and the protein used as an immunogen in mice, the antibody thus produced reacts with P39.5 of IP90. Other gene fragments, designated, 1-1, 3-1, 6-1, 9-1 and 12-1, from *Borrelia garinii* strain IP90 were similarly each inserted in pBluescript II plasmids, transformed in *E. coli* and deposited. These latter deposits were made with the ATCC on Jun. 10, 1998 under Accession Nos. 98768 for 1-1, 98769 for 3-1, 98770 for 6-1, 98771 for 9-1 and 98772 for 12-1. All deposits were all made to meet the requirements of the Budapest Treaty on the International Recognition of the Deposit of Microorganisms for the Purpose of Patent Procedure, and fully comply with the requirements of the United States Patent and Trademark Office for deposits for patent purposes. Sequences useful in the present invention may be obtained from these deposits.

A. Nucleic Acid Sequences

The present invention provides mammalian nucleic acid sequences encoding fragments of P39.5. The nucleic acid sequences of this invention are isolated from cellular materials with which they are naturally associated. As described in the examples below, a segment of 1190 bp which encodes a portion of the coding region of the Borrelia P39.5 gene was cloned and sequenced. It encompasses a single open reading frame that encodes a putative 37.7 kDa protein. This partial DNA sequence is reported in SEQ ID NOS: 13 and 1. SEQ ID NO: 13 is a sequence immediately 5' to the first base of SEQ ID NO: 1. Together these sequences from a partial protein of 1189 bp and about 396 amino acids. The sequenced fragment is composed of mostly hydrophilic domains that contain several internally repeated regions and a unique region spanning about bp 627 to about bp 712 of SEQ ID NO: 1. See, FIG. 2, which identifies the repeated sequences and identifies the homologies and percent identities of such sequences.

Where in this text, protein and/or DNA sequences are defined by their percent homologies or identities to identified sequences, the algorithms used to calculate the percent identities or percent similarities include the following: the Smith-Waterman algorithm [J. F. Collins et al, 1988, *Comput. Appl. Biosci.,* 4:67–72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp.417], and the BLAST and FASTA programs [E. G. Shpaer et al, 1996, *Genomics,* 38:179–191]. These references are incorporated herein by reference.

Also encompassed within this invention are other Borrelia nucleic acid fragments, e.g., cassette string fragments, as well as fragments of P39.5. Such fragments are referred to as 1-1 (which encodes a protein/peptide P1-1), 3-1 (which encodes a protein/peptide P3-1), 6-1 (which encodes a protein/peptide P6-1), 9-1 (which encodes a protein/peptide P9-1) and 12-1 (which encodes a protein/peptide P12-1). Preferably, such fragments are characterized by encoding a biologically active portion of P39.5, e.g., an epitope. Generally, these oligonucleotide fragments are at least 15 nucleotides in length. However, oligonucleotide fragments of varying sizes may be selected as desired. Such fragments may be used for such purposes as performing polymerase chain reaction (PCR), e.g., on a biopsied tissue sample. For example, useful fragments of P39.5 DNA and corresponding sequences comprise sequences occurring between bp 793–816 of SEQ ID NO: 1 and bp 59–85 of SEQ ID NO: 13. Other useful fragments are identified in FIG. 2. Fragments of 1-1 include sequences of SEQ ID NOS: 3, 4 and 5. Fragments of 3-1 include sequences of SEQ ID NOS: 6 and 7; fragments of 6-1 include sequences of SEQ ID NOS: 8 and 9. A fragment of 9-1 includes the sequence of SEQ ID NO: 10. Fragments of 12-1 include the sequences of SEQ ID NOS: 11 and 12. The complete sequences of 1-1, 3-1, 6-1, 9-1 and 12-1 and other useful fragments may be readily obtained by one of skill in the art by resort to conventional DNA sequencing techniques applied to the DNA deposited with the ATCC above.

The DNA sequences of SEQ ID NOS: 1 and 3–12 as well as the deposited materials identified above permit one of skill in the art to readily obtain the corresponding anti-sense strands of these DNA sequences. Further, using known techniques, one of skill in the art can readily obtain additional genomic and cDNA sequences which flank the illustrated DNA sequences or the corresponding RNA sequences, as desired. Similarly the availability of SEQ ID NOS: 1 and 3–12 and the deposited materials of this invention permits one of skill in the art to obtain other species P39.5 analogs, *B. garinii* peptides, and fragments thereof, by use of the nucleic acid sequences of this invention as probes in a conventional technique, e.g., polymerase chain reaction. Allelic variants of these sequences within a species (i.e., sequences containing some individual nucleotide differences from a more commonly occurring sequence within a species, but which nevertheless encode the same protein or a protein with the same function) such as other variants of P39.5 SEQ ID NO: 2, may also be readily obtained given the knowledge of this sequence provided by this invention.

The present invention further encompasses nucleic acid sequences capable of hybridizing under stringent conditions [see, J. Sambrook et al, *Molecular Cloning: A Laboratory Manual,* 2d ed., Cold Spring Harbor Laboratory (1989)] to the sequences of SEQ ID NO: 1, their anti-sense strands, or biologically active fragments thereof. An example of a highly stringent hybridization condition is hybridization at 2×SSC at 65° C., followed by a washing in 0.1×SSC at 65° C. for an hour. Alternatively, an exemplary highly stringent hybridization condition is in 50% formamide, 4×SSC at 42° C. Moderately high stringency conditions may also prove useful, e.g., hybridization in 4×SSC at 55° C., followed by washing in 0.1×SSC at 37° C. for an hour. An alternative exemplary moderately high stringency hybridization condition is in 50% formamide, 4×SSC at 30° C.

According to the invention, the nucleic acid sequences may be modified. Utilizing the sequence data of SEQ ID NOS: 1 and 3–12, it is within the skill of the art to obtain or prepare synthetically or recombinantly other polynucleotide sequences, or modified polynucleotide sequences, encoding the full-length proteins or useful fragments of the invention. Such modifications at the nucleic acid level include, for example, modifications to the nucleotide sequences which are silent or which change the amino acids, e.g. to improve expression or secretion. Also included are allelic variations, caused by the natural degeneracy of the genetic code.

Also encompassed by the present invention are mutants of the P39.5 fragments and cassette string sequences 1-1, 3-1, 6-1, 7-1, 9-1 and 12-1 provided herein. Such mutants include amino terminal, carboxy terminal or internal deletions, which substantially retain the antigenicity of the full-length P39.5 or other proteins or fragments. Such a truncated, or deletion, mutant may be expressed for the purpose of affecting the activity of the full-length or wild-type gene or gene fragments.

These nucleic acid sequences are useful for a variety of diagnostic, prophylactic and therapeutic uses. Advantageously, the nucleic acid sequences are useful in the development of diagnostic probes and antisense probes for use in the detection and diagnosis of Lyme disease by utilizing a variety of known nucleic acid assays, e.g., Northern and Southern blots, polymerase chain reaction (PCR), and other assay techniques known to one of skill in the art. The nucleic acid sequences of this invention are also useful in the production of P39.5 proteins and homologs as well as other proteins of *B. garinii.*

The nucleotide sequences of the invention may be isolated by conventional uses of polymerase chain reaction or cloning techniques such as those described in conventional texts such as Sambrook et al, cited above. For example, the nucleic acid sequences of the antigen of this invention may be prepared or isolated from *B. garinii* DNA using DNA primers and probes and PCR techniques. Alternatively, the antigen may be obtained from gene banks derived from *B. garinii* whole genomic DNA. These sequences, fragments thereof, modifications thereto and the full-length sequences may be constructed recombinantly using conventional genetic engineering or chemical synthesis techniques or PCR, and the like by utilizing the information provided herein.

B. Protein Sequences

The present invention also provides *B. burgdorferi* sensu lato proteins, such as *B. garinii* proteins and peptides, including P39.5 polypeptides or proteins, and the peptides/proteins represented by the designations P1-1, P3-1, P6-1, P7-1, P9-1 and P12-1 of this invention. These proteins are free from association with other contaminating proteins or materials with which they are found in nature. Because the native P39.5 was fully extracted into the detergent phase in a Triton-X114 extraction, it is likely a lipoprotein. The P39.5 antigen has a relative molecular mass of 39,500 daltons as measured by Western immunoblot (See Example 2 and FIG. 6). In one embodiment, the invention provides a partial P39.5 [SEQ ID NO:2] polypeptide of about 354 amino acids, likely a lipoprotein, having a predicted relative molecular mass of about 37.7 kD (i.e., "the P7-1 fragment"). This deduced amino acid sequence [SEQ ID NO: 2] is up to 22% identical to members of the variable major protein (Vmp) family of outer surface lipoproteins of *Borrelia hermsii* (see Example 6). It is about 50% identical to the Vmp-like sequence (vls) VlsE of the B31 strain of *B. burgdorferi* [J.-R. Zhang et al, cited above] and to other vls sequences of *B. burgdorferi* [i.e., Vls-6 Genbank no. U76406 (53% identity over 190 aa); VlsE Genbank no. U84553 (57% over 210 aa) and U84566 (58% over 209 aa) and U84555 (58% over 210 aa)].

VlsE is part of an antigen of *B. burgdorferi* that undergoes antigenic variation by a mechanism of recombination whereby a central fragment of the expressed copy (VlsE) is recombined with fragments from a string of 15 "cassettes" located upstream from the expressed copy [J. Zhang, cited above]. Each cassette is on average 500 bp in length, and the whole string occupies a stretch of DNA of about 8 kb. One of the remarkable features of this string of cassettes is that in *B. burgdorferi* B31, the cassettes are arranged in a nearly contiguous open reading frame interrupted only by a stop codon in cassette vls11 and two frame shifts in cassettes vls14 and vls16. See, e.g., FIG. 6, which is a copy of a similar structure defined in Zhang et al, cited above.

A longer partial protein sequence of P39.5 is formed by the direct fusion of the partial sequence from clone 14 [SEQ ID NO: 14] to the 5' end of the sequence of SEQ ID NO: 2. The identification of the sequence from clone 14 as a sequence 5' to the sequence of P7-1 resulting from overlapping sequences between the two clones from which these sequences were obtained, which overlapping sequences demonstrated that they were part of the same open reading frame. Thus the Leu (amino acid 47 of SEQ ID NO: 14) is immediately followed by the Lys (amino acid 1 of SEQ ID NO: 2) in the larger P39.5 deduced amino acid sequence.

The present invention provides partial DNA and deduced amino acid sequences of several fragments which appear to be part of the cassette string of *B. garinii* IP90. These fragments, which may include 7-1, are named 1-1, 3-1, 6-1, 9-1, and 12-1, and are between 1 and 2 kb in length. Each of them expresses a peptide (off of the lacZ promoter of pBluescript) which is commensurate with the size of the insert and which reacts with antibody from infected monkeys. None of the 5' ends of these fragments [SEQ ID NOS: 1, 3, 6, 8, 10 and 11] contains a hydrophobic leader or a signal peptidase II consensus sequence of the type that is characteristic of bacterial lipoproteins. These fragments must therefore be part of the cassette string of IP90 and, like the cassette string of B31, they are in-frame. These vls-like proteins are identified by partial 5' and 3' sequences [see, e.g., SEQ ID NOS: 1, 3, 5 through 12]. One of skill in the art using conventional techniques, such as PCR, may readily use the partial 5' and 3' sequences provided herein and the DNA sequences of (or DNA library of) *B. garinii* or the materials deposited with the ATCC for each cassette string protein identified above, to identify the complete sequences thereof. Such methods are routine and not considered to require undue experimentation, given the information provided herein.

Antigens of this invention may be characterized by immunological measurements including, without limitation, western blot, macromolecular mass determinations by biophysical determinations, such as SDS-PAGE/staining, HPLC and the like, antibody recognition assays, T-cell recognition assays, MHC binding assays, and assays to infer immune protection or immune pathology by adoptive transfer of cells, proteins or antibodies.

The proteinaceous P39.5 surface antigen of this invention (as well as its naturally occurring variants or analogs in other species of Borrelia or the other Vls-like proteins identified herein) may be isolated in the form of a complete intact protein, or a polypeptide or fragment thereof. In one embodiment, P39.5 is isolated by immunoblot procedures according to its respective molecular mass, as described below in Example 5. Such isolation provides the antigen in a form substantially free from other proteinaceous and non-proteinaceous materials of the microorganism and the tick vector. The molecules comprising the Borrelia polypeptides and antigens of this invention may be isolated from the spirochete and further purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

Alternatively, the amino acid sequences of P39.5 or the other Borrelia proteins of this invention may be produced recombinantly following conventional genetic engineering techniques [see e.g., Sambrook et al, cited above and the detailed description of making the proteins below].

i. Analogs/Modified Antigens

Also included in the invention are analogs, or modified versions, of the P39.5 protein or vls-like proteins P1-1, P3-1, P6-1, P7-1, P9-1 and P12-1, provided herein. Typically, such analogs differ from the specifically identified proteins by only one to four codon changes. Examples include polypeptides with minor amino acid variations from the illustrated partial amino acid sequence of, for example, P7-1 (SEQ ID NO: 2), in particular, conservative amino acid replacements. Conservative replacements are those that take place within a family of amino acids that are related in their side chains and chemical properties. Also provided are homologs of the proteins of the invention which are characterized by having at least 85% identity with SEQ ID NO:2 or with the sequences of the vls-like proteins. Based on the sequence information provided herein, one of skill in the art can readily obtain full-length P7-1 or P7-1 homologs and analogs, as well as the full-length viselike 1-1, 3-1, 6-1, 9-1 and 12-1 protein homologs and analogs from other bacterial species.

An antigen of the present invention may also be modified to increase its immunogenicity. For example, the antigen may be coupled to chemical compounds or immunogenic carriers, provided that the coupling does not interfere with the desired biological activity of either the antigen or the carrier. For a review of some general considerations in coupling strategies, see *Antibodies, A Laboratory Manual*, Cold Spring Harbor Laboratory, ed. E. Harlow and D. Lane (1988). Useful immunogenic carriers known in the art, include, without limitation, keyhole limpet hemocyanin (KLH); bovine serum albumin (BSA), ovalbumin, PPD (purified protein derivative of tuberculin); red blood cells; tetanus toxoid; cholera toxoid; agarose beads; activated carbon; or bentonite. Useful chemical compounds for coupling include, without limitation, dinitrophenol groups and arsonilic acid.

The antigen may also be modified by other techniques, such as denaturation with heat and/or SDS.

ii. Fragments/Deletion Mutants

Further encompassed by this invention are additional fragments of the P39.5 polypeptide, the P7-1 peptide or of the other vls-like proteins identified herein. Such fragments are desirably characterized by having a biological activity similar to that displayed by the complete protein, including, e.g., the ability to induce antibodies to the causative agent of Lyme Disease. These fragments may be designed or obtained in any desired length, including as small as about 5–8 amino acids in length. Such a fragment may represent an epitope of the protein.

The internal repeats of P39.5 (see FIG. 2) indicate that this protein, like OspA, may undergo homologous recombinations in Borrelia which may lead to mutants expressing shortened, partially-deleted versions of the gene. Thus, the P7-1 protein [SEQ ID NO: 2] of the invention may be modified to create deletion mutants, for example, by truncation at the amino or carboxy termini, or by elimination of one or more amino acids. Deletion mutants of P7-1 created by homologous recombination of its repeat sequences (FIG. 2) are also encompassed by this invention, as are the DNA sequences encoding them. In certain deletion mutants, portions of the P39.5 coding region, described above, e.g., regions IIA, IIB, and B, are deleted.

Deletion mutants of the P39.5 antigens that, like P39.5 and unlike OspA, are expressed in vivo, will likely be killed upon infection of the vertebrate host. Most OspA deletion mutants escape killing with anti-OspA antibody in the absence of complement, but are killed by this antibody and complement acting together. Since anti-OspA antibody kills spirochetes in the tick midgut (where OspA is expressed, but complement is likely not active), OspA deletion mutants may escape the anti-Osp A antibody elicited by the OspA vaccine. In contrast, since P39.5 is expressed in vivo, where complement and anti-P39.5 antibody are both present, P39.5 deletion mutants may not escape a P39.5 based vaccine.

Still other modified fragments of P39.5, P1-1, P3-1, P6-1, P7-1, P9-1, or P12-1 may be prepared by any number of now conventional techniques to improve production thereof, to enhance protein stability or other characteristics, e.g. binding activity or bioavailability, or to confer some other desired property upon the protein. Other useful fragments of these polypeptides may be readily prepared by one of skill in the art using known techniques, such as deletion mutagenesis and expression.

iii. Fusion or Multimeric Proteins and Compositions

The P39.5 protein of the present invention, or fragments of it, as well as the vls-like cassette string proteins or fragments thereof, may also be constructed, using conventional genetic engineering techniques as part of a larger and/or multimeric protein or protein compositions. Antigens of this invention may be in combination with *B. burgdorferi* outer surface proteins, such as OspA and OspB, or various fragments of the antigens described herein may be in combination with each other. In such a combination, the antigen may be in the form of a fusion protein. The antigen of the invention may be optionally fused to a selected polypeptide or protein, e.g. Borrelia antigens OspA and OspB, other Borrelia antigens, and proteins or polypeptides derived from other microorganisms. For example, an antigen or polypeptide of this invention may be fused at its N-terminus or C-terminus to OspA polypeptide, or OspB polypeptide or to a non-OspA non-OspB polypeptide or combinations thereof OspA and OspB polypeptides which may be useful for this purpose include polypeptides identified by the prior art [see, e.g. PCT/US91/04056] and variants thereof Non-OspA, non-OspB polypeptides which may be useful for this purpose include polypeptides of the invention and those identified by the prior art, including, the *B. burgdorferi*, flagella-associated protein and fragments thereof, other *B. burgdorferi* proteins and fragments thereof, and non-*B. burgdorferi* proteins and fragments thereof.

Still another fusion protein of this invention is provided by expressing the DNA molecule formed by the P39.5 DNA sequence or a fragment thereof fused to DNA fragments that are homologous (25–95% identity) to P39.5. One example of such a protein comprises the amino acid sequence of SEQ ID NO: 2 to which is fused amino acid fragments that are up to 95% identical to that sequence. These fragments may be inserted in any order and may contain repeated sequences such as those depicted in FIG. 2. These long strings of DNA that form a single open reading frame may be constructed from P39.5 homologs, including P39.5, or be derived from the naturally occurring long open reading frames, such as one or more of the vls cassette proteins. The vls cassette proteins from *B. garinii* (e.g., the proteins designated P1-1, P3-1, P6-1, P9-1 and/or P12-1) may be fused to each other and/or inserted into the P39.5 or P7-1 DNA sequence, thereby creating a large DNA molecule which expresses a protein which may stimulate a variety of antibody specificities.

These fusion proteins comprising multiple polypeptides of this invention are constructed for use in the methods and compositions of this invention. These fusion proteins or multimeric proteins may be produced recombinantly, or may be synthesized chemically. They also may include the polypeptides of this invention fused or coupled to moieties other than amino acids, including lipids and carbohydrates. Further, antigens of this invention may be employed in combination with other Borrelia vaccinal agents described by the prior art, as well as with other species of vaccinal agents derived from other viruses. Such proteins are effective in the prevention, treatment and diagnosis of Lyme disease as caused by a wide spectrum of *B. burgdorferi* isolates.

A protein composition which may be a preferred alternative to the fusion proteins described above is a cocktail (i.e., a simple mixture) containing different P39.5 proteins or fragments, or different mixtures of the cassette string proteins of this invention. Such mixtures of these proteins or antigenic fragments thereof are likely to be useful in the generation of desired antibodies to *B. garinii*.

iv. Salts

An antigen of the present invention may also be used in the form of a pharmaceutically acceptable salt. Suitable acids and bases which are capable of forming salts with the polypeptides of the present invention are well known to those of skill in the art, and include inorganic and organic acids and bases.

II. Methods of Making Antigens and Nucleic Acid Sequences of the Invention

A. Expression In Vitro

To produce recombinant P7-1 and/or other cassette string proteins or other fragments of P39.5 of this invention, the DNA sequences of the invention are inserted into a suitable expression system. Desirably, a recombinant molecule or vector is constructed in which the polynucleotide sequence encoding the selected protein, e.g., P7-1, is operably linked to a heterologous expression control sequence permitting expression of the protein. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. See, Sambrook et al, *Molecular Cloning. A Laboratory Manual,* 2d edition, Cold Spring Harbor Laboratory, New York (1989); Miller et al, *Genetic Engineering,* 8:277–298 (Plenum Press 1986) and references cited therein.

Suitable host cells or cell lines for transfection by this method include bacterial cells. Preferably, at least for use of the P39.5 protein which is believed to be a lipoprotein (e.g., see Example 5), the selected protein is expressed in bacteria, which have the cellular machinery to attach lipids. This expression system is especially preferred where the protein is being expressed for use as a vaccine or therapeutic. For example, the various strains of *E. coli* (e.g., HB101, MC1061, and strains used in the following examples) are well-known as host cells in the field of biotechnology. Various strains of *B. subtilis,* Pseudomonas, Streptomyces, and other bacilli and the like are also be employed in this method.

Many strains of yeast cells known to those skilled in the art are also available as host cells for expression of the polypeptides of the present invention. Other fungal cells may also be employed as expression systems. Although yeast can also lipidate proteins, the lipidation pattern may be different from bacteria, i.e., different from the native protein.

Mammalian cells, such as human 293 cells, Chinese hamster ovary cells (CHO), the monkey COS-1 cell line or murine 3T3 cells derived from Swiss, Balb-c or NIH mice are used. Another suitable mammalian cell line is the CV-1 cell line. Still other suitable mammalian host cells, as well as methods for transfection, culture, amplification, screening, production, and purification are known in the art. [See, e.g., Gething and Sambrook, *Nature,* 293:620–625 (1981), or alternatively, Kaufman et al, *Mol. Cell. Biol.,* 5(7):1750–1759 (1985) or Howley et al, U.S. Pat. No. 4,419,446].

Alternatively, insect cells such as *Spodoptera frugipedera* (Sf9) cells may be used.

Thus, the present invention provides a method for producing a recombinant Borrelia protein, e.g., P7-1 or other cassette string proteins, which involves transfecting, e.g., by conventional means such as electroporation, a host cell with at least one expression vector containing a polynucleotide of the invention under the control of a transcriptional regulatory sequence. The transfected or transformed host cell is then cultured under conditions that allow expression of the protein. The expressed protein is recovered, isolated, and optionally purified from the cell (or from the culture medium, if expressed extracellularly) by appropriate means known to one of skill in the art.

For example, the proteins are isolated in soluble form following cell lysis, or extracted using known techniques, e.g., in guanidine chloride. If desired, the proteins or fragments of the invention are produced as a fusion protein. Such fusion proteins are those described above. Alternatively, for example, it may be desirable to produce fusion proteins to enhance expression of the protein in a selected host cell, to improve purification, or for use in monitoring the presence of the desired protein, e.g., P7-1, in tissues, cells or cell extracts. Suitable fusion partners for the proteins of the invention are well known to those of skill in the art and include, among others, β-galactosidase, glutathione-S-transferase, and poly-histidine.

B. Expression In Vivo

Alternatively, where it is desired that the P7-1 or other cassette string protein of the invention (whether full-length or a desirable fragment) be expressed in vivo, e.g., to induce antibodies, or as a DNA vaccine, an appropriate vector for delivery is readily selected by one of skill in the art. Exemplary vectors for in vivo gene delivery are readily available from a variety of academic and commercial sources, and include, e.g., adeno-associated virus [International patent application No. PCT/US91/03440], adenovirus vectors [M. Kay et al, *Proc. Natl. Acad. Sci. USA,* 91:2353 (1994); S. Ishibashi et al, *J. Clin. Invest.,* 92:883 (1993)], or other viral vectors, e.g., various poxviruses, vaccinia, etc. Methods for insertion of a desired gene, e.g., P7-1, and obtaining in vivo expression of the encoded protein, are well known to those of skill in the art.

III. Antibodies of the Invention

The present invention also provides antibodies capable of recognizing and binding the isolated, or modified, or multimeric antigens of this invention, including antibodies derived from mixtures of such antigens or fragments thereof. These antibodies are useful in diagnosis of Lyme disease and in therapeutic compositions for treating humans and/or animals that test positive for, or, prior to testing, exhibit symptoms of, Lyme Disease. The antibodies are useful in diagnosis alone or in combination with antibodies to other antigens of this invention as well as antibodies to other known *B. burgdorferi* antigens. These antibodies are also useful in passive vaccine compositions.

The antibodies of this invention are generated by conventional means utilizing the isolated, recombinant or modified antigens of this invention, or mixtures of such antigens or antigenic fragments. For example, polyclonal antibodies are generated by conventionally stimulating the immune system of a selected animal or human with the isolated antigen or mixture of antigenic proteins or peptides of this invention, allowing the immune system to produce natural antibodies thereto, and collecting these antibodies from the animal or human's blood or other biological fluid.

For example, an antibody according to the invention is produced by administering to a vertebrate host the antigen or antigenic composition of this invention, e.g., P7-1. Preferably a recombinant version of P7-1 (rP7-1) is used as an immunogen. A suitable polyclonal antibody against the P7-1 antigen kills IP90 spirochetes in vitro by antibody-dependent, complement-mediated killing (ADCK) regardless of whether the antibody was obtained by: (1) affinity purification using as immunoabsorbant native P39.5 antigen of IP90 spirochetes (as separated on a Western blot; see FIG. 6) and as source of antibody the antiserum generated during an infection of rhesus monkeys with JD1 spirochetes or, (2) by immunizing mice with recombinant P7-1 from IP90 (rP7-1).

Thus, an antibody of the invention is isolated by affinity purifying antiserum generated during an infection of a vertebrate animal, e.g., a rhesus monkey, with JD1 spirochetes, using as immunoabsorbant the native P39.5 antigen of IP90, or one or more of the cassette string proteins identified herein. Similarly, an antibody of the invention is isolated by immunizing mice with a purified, recombinant antigen of this invention, or a purified, isolated P39.5 of native origin. Monoclonal antibodies (MAbs) directed against P39.5 are also generated. Hybridoma cell lines expressing desirable MAbs are generated by well-known conventional techniques, e.g. Kohler and Milstein and the many known modifications thereof Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., *Science* 233:747–753 (1986); Queen et al., *Proc. Nat'l. Acad. Sci. USA*, 86:10029–10033 (1989); PCT Patent Publication No. WO9007861; Riechmann et al., *Nature*, 332:323–327 (1988); Huse et al, *Science*, 246:1275–1281 (1988)].

Given the disclosure contained herein, one of skill in the art may generate chimeric, humanized or fully human antibodies directed against P39.5 or the cassette proteins, or antigenic fragments thereof by resort to known techniques by manipulating the complementarity determining regions of animals or human antibodies to the antigen of this invention. See, e.g., E. Mark and Padlin, "Humanization of Monoclonal Antibodies", Chapter 4, *The Handbook of Experimental Pharmacology,* Vol. 113, The Pharmacology of Monoclonal Antibodies, Springer-Verlag (June, 1994).

Alternatively, the antigens are assembled as multi-antigenic complexes [see, e.g., European Patent Application No. 0339695, published Nov. 2, 1989] or as simple mixtures of antigenic proteins/peptides and employed to elicit high titer antibodies capable of binding the selected antigen(s) as it appears in the biological fluids of an infected animal or human.

Further provided by the present invention are anti-idiotype antibodies (Ab2) and anti-anti-idiotype antibodies (Ab3). Ab2 are specific for the target to which anti-P39.5 antibodies of the invention bind and Ab3 are similar to P39.5 antibodies (Ab1) in their binding specificities and biological activities [see, e.g., M. Wettendorff et al., "Modulation of anti-tumor immunity by anti-idiotypic antibodies." In *Idiotypic Network and Diseases,* ed. by J. Cerny and J. Hiernaux J, Am. Soc. Microbiol., Washington D.C.: pp. 203–229, (1990)]. These anti-idiotype and anti-anti-idiotype antibodies are produced using techniques well known to those of skill in the art. Such anti-idiotype antibodies (Ab2) can bear the internal image of P39.5, the cassette proteins, or fragments thereof and are thus useful for the same purposes as P39.5, the cassette proteins or the fragments.

In general, polyclonal antisera, monoclonal antibodies and other antibodies which bind to the selected antigen (Ab1) are useful to identify epitopes of P39.5 or the cassette proteins to separate P39.5 (or the cassette proteins) and analogs thereof from contaminants in living tissue (e.g., in chromatographic columns and the like), and in general as research tools and as starting material essential for the development of other types of antibodies described above. Anti-idiotype antibodies (Ab2) are useful for binding the same target and thus may be used in place of the original antigen, e.g., P39.5, to induce an immune response. The Ab3 antibodies are useful for the same reason the Ab1 are useful. Other uses as research tools and as components for separation of P39.5 or the cassette proteins, from other contaminants, for example, are also contemplated for the above-described antibodies.

For use in diagnostic assays, the antibodies are associated with conventional labels which are capable, alone or in concert with other compositions or compounds, of providing a detectable signal. Where more than one antibody is employed in a diagnostic method, the labels are desirably interactive to produce a detectable signal. Most desirably, the label is detectable visually, e.g. calorimetrically. A variety of enzyme systems have been described in the art which will operate to reveal a colorimetric signal in an assay. As one example, glucose oxidase (which uses glucose as a substrate) releases peroxide as a product. Peroxidase, which reacts with peroxide and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength. Other label systems that may be utilized in the methods of this invention are detectable by other means, e.g., colored latex microparticles [Bangs Laboratories, Indiana] in which a dye is embedded may be used in place of enzymes to form conjugates with the antibodies and provide a visual signal indicative of the presence of the resulting complex in applicable assays. Still other labels include fluorescent compounds, radioactive compounds or elements. Detectable labels for attachment to antibodies useful in diagnostic assays of this invention may be easily selected from among numerous compositions known and readily available to one skilled in the art of diagnostic assays. The methods and antibodies of this invention are not limited by the particular detectable label or label system employed.

IV. Diagnostic Methods and Assays

The present invention also provides methods of diagnosing Lyme disease. These diagnostic methods are useful for diagnosing humans or animals exhibiting the clinical symptoms of, or suspected of having, Lyme disease.

In one embodiment, this diagnostic method involves detecting the presence of naturally occurring anti-P39.5 antibodies which are produced by the infected human or animal patient's immune system in its biological fluids, and which are capable of binding to the antigens of this invention or combinations thereof This method comprises the steps of incubating a P39.5 antigen or a cassette string antigen of this invention with a sample of biological fluids from the patient. Antibodies present in the fluids as a result of *B. burgdorferi* infection will form an antibody-antigen complex with the antigen. Subsequently the reaction mixture is analyzed to determine the presence or absence of these antigen-antibody complexes. The step of analyzing the reaction mixture comprises contacting the reaction mixture with a labeled specific binding partner for the antibody.

In a similar embodiment, this diagnostic method involves detecting the presence of naturally occurring anti-P1-1, anti-P3-1, anti-P6-l, anti P7-i, anti-P9-1, and/or anti-P12-1 antibodies which are produced by the infected human or animal patient's immune system in its biological fluids, and which are capable of binding to the antigens of this invention or combinations thereof This method comprises the steps of incubating one or preferably, a mixture, of these antigen(s) of this invention with a sample of biological fluids from the patient. Antibodies present in the fluids as a result of *B. burgdorferi* infection will form antibody-antigen complexes with the antigen(s). Subsequently the reaction mixture is analyzed to determine the presence or absence of these antigen-antibody complexes. The step of analyzing the reaction mixture comprises contacting the reaction mixture with a labeled specific binding partner for the antibody.

In one embodiment of the method, purified antigen, fragment or mixture of antigens is electro- or dot-blotted onto nitrocellulose paper. Subsequently, the biological fluid (e.g. serum or plasma) is incubated with the blotted antigen, and antibody in the biological fluid is allowed to bind to the antigen(s). The bound antibody is then detected by standard immunoenzymatic methods.

In another embodiment of the method, latex beads are conjugated to the antigen(s) of this invention. Subsequently, the biological fluid is incubated with the bead/protein conjugate, thereby forming a reaction mixture. The reaction mixture is then analyzed to determine the presence of the antibodies.

In another embodiment, the diagnostic method of the invention involves detecting the presence of the naturally occurring P39.5 or cassette string antigen(s) itself in its association with the Borrelia pathogen in the biological fluids of an animal or human infected by the pathogen. This method includes the steps of incubating an antibody of this invention (e.g. Produced by administering to a suitable human and/or animal an antigen of this invention preferably conventionally labelled for detection) with a sample of biological fluids from a human or an animal to be diagnosed. In the presence of Borrelia infection of the human or animal patient, an antigen-antibody complex is formed (specific binding occurs). Subsequently, excess labeled antibody is optionally removed, and the reaction mixture is analyzed to determine the presence or absence of the antigen-antibody complex and the amount of label associated therewith.

Assays employing a protein antigen of the invention can be heterogenous (i.e., requiring a separation step) or homogenous. If the assay is heterogenous, a variety of separation means can be employed, including centrifugation, filtration, chromatography, or magnetism.

One preferred assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-B. burgdorferi antibody. The sample can be applied neat, or more often, it can be diluted, usually in a buffered solution which contains a small amount (0.1–5.0% by weight) of protein, such as BSA, NGS, or BLOTTO. After incubating for a sufficient length of time to allow specific binding to occur, the well is washed to remove unbound protein and then incubated with labeled anti-human immunoglobulin ($\alpha$ HuIg) or labeled antibodies to other species, e.g., dogs. The label can be chosen from a variety of enzymes, including horseradish peroxidase (HRP), $\beta$-galactosidase, alkaline phosphatase, and glucose oxidase, as described above. Sufficient time is allowed for specific binding to occur again, then the well is washed again to remove unbound conjugate, and the substrate for the enzyme is added. Color is allowed to develop and the optical density of the contents of the well is determined visually or instrumentally.

Further, MAbs or other antibodies of this invention which are capable of binding to the antigen(s) can be bound to ELISA plates. In another diagnostic method, the biological fluid is incubated on the antibody-bound plate and washed. Detection of any antigen-antibody complex, and qualitative measurement of the labeled MAb is performed conventionally, as described above.

Other useful assay formats include the filter cup and dipstick. In the former assay, an antibody of this invention is fixed to a sintered glass filter to the opening of a small cap. The biological fluid or sample (5 mL) is worked through the filter. If the antigen is present (i.e., B. burgdorferi infection), it will bind to the filter which is then visualized through a second antibody/detector. The dipstick assay involves fixing an antigen or antibody to a filter, which is then dipped in the biological fluid, dried and screened with a detector molecule.

Other diagnostic assays can employ the antigen(s) or fragments of this invention as nucleic acid probes or an anti-sense sequences, which can identify the presence of infection in the biological fluid by hybridizing to complementary sequences produced by the pathogen in the biological fluids. Such techniques, such as PCR, Northern or Southern hybridizations etc. are well known in the art.

It should be understood by one of skill in the art that any number of conventional protein assay formats, particularly immunoassay formats, or nucleic acid assay formats, may be designed to utilize the isolated antigens and antibodies or their nucleic acid sequences or anti-sense sequences of this invention for the detection of Borrelia infection in animals and humans. This invention is thus not limited by the selection of the particular assay format, and is believed to encompass assay formats which are known to those of skill in the art.

V. Diagnostic Kits

For convenience, reagents for ELISA or other assays according to this invention may be provided in the form of kits. Such kits are useful for diagnosing infection with Borrelia in a human or an animal sample. Such a diagnostic kit contains an antigen of this invention and/or at least one antibody capable of binding an antigen of this invention, or the nucleic acid sequences encoding them, or their anti-sense sequences. Alternatively, such kits may contain a simple mixture of such antigens or sequences, or means for preparing a simple mixture.

These kits can include microtiter plates to which the Borrelia antigen proteins or antibodies or nucleic acid sequences of the invention have been pre-adsorbed, various diluents and buffers, labeled conjugates for the detection of specifically bound antigens or antibodies, or nucleic acids and other signal-generating reagents, such as enzyme substrates, cofactors and chromogens. Other components of these kits can easily be determined by one of skill in the art. Such components may include polyclonal or monoclonal capture antibodies, antigen of this invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for calorimetric comparisons, disposable gloves, decontamination instructions, applicator sticks or containers, and a sample preparator cup. Such kits provide a convenient, efficient way for a clinical laboratory to diagnose Borrelia infection.

VI. Therapeutic Compositions

The antigens, antibodies, nucleic acid sequences or anti-sense sequences of the invention, alone or in combination with other antigens, antibodies, nucleic acid sequences or anti-sense sequences may further be used in therapeutic compositions and in methods for treating humans and/or animals with Lyme Disease. For example, one such therapeutic composition may be formulated to contain a carrier or diluent and one or more of the anti-P7–1 or other anti-cassette string protein antibodies of the invention. Suitable pharmaceutically acceptable carriers facilitate administration of the proteins but are physiologically inert and/or nonharmful.

Carriers may be selected by one of skill in the art. Exemplary carriers include sterile saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

Optionally, this composition may also contain conventional pharmaceutical ingredients, such as preservatives, or chemical stabilizers. Suitable ingredients which may be used in a therapeutic composition in conjunction with the antibodies include, for example, casamino acids, sucrose, gelatin, phenol red, N-Z amine, monopotassium diphosphate, lactose, lactalbumin hydrolysate, and dried milk.

Alternatively, or in addition to the antibodies of the invention, other agents useful in treating Lyme disease, e.g., antibiotics or immunostimulatory agents and cytokine regulation elements, are expected to be useful in reducing or eliminating disease symptoms. Agents which can be used to suppress or counteract the immune suppressants released by the tick vector or the spirochete should act to assist the natural immunity of the infected human or animal. Thus, such agents may operate in concert with the therapeutic compositions of this invention. The development of therapeutic compositions containing these agents is within the skill of one in the art in view of the teachings of this invention.

According to the method of the invention, a human or an animal may be treated for Lyme Disease by administering an effective amount of such a therapeutic composition. An "effective amount" may be between about 0.05 to about 1000 $\mu$g/mL of an antibody of the invention. A suitable dosage may be about 1.0 mL of such an effective amount. Such a composition may be administered 1–3 times per day over a 1 day to 12 week period. However, suitable dosage adjustments may be made by the attending physician or veterinarian depending upon the age, sex, weight and general health of the human or animal patient. Preferably, such a composition is administered parenterally, preferably intramuscularly or subcutaneously. However, it may also be formulated to be administered by any other suitable route, including orally or topically.

VII. Vaccine Compositions

None of the potential problems of the prior art arise with a vaccine based on an antigen which is expressed in the vertebrate host. An improved surface-antigen-based vaccine for the prevention of Lyme disease in humans and other animals is provided by the inclusion of the P39.5 antigen of this invention, and a pharmaceutically acceptable carrier or diluent. This vaccine composition may contain one or more of the isolated, recombinant, modified or multimeric forms of the P39.5 antigen of the invention, or mixtures thereof. Similarly, salts of the antigenic proteins may be employed in such compositions.

Another embodiment of a composition of the present invention is based on the other cassette string antigens, i.e., P1-1, P3-1, P6-1, P7-1, P9-1 and P12-1. The inventor proposes that the mechanism of antigenic variation to which the vlsE antigen is subjected indicates that this antigen is crucially important for spirochetal survival in the vertebrate host. According to this invention, a novel vaccine method involves circumventing the spirochetal defense mechanism by immunizing a host with a large fraction of the epitopes that are expressed on the cassette string that is the very source of the variation. This is made possible by the unique fact that most of this cassette string is in frame. The inventors have demonstrated this concept, as described in the Examples below, by immunizing a host with the cassette string antigen, P7-1, and inducing antibody that kills the spirochetes. Thus, according to this invention, one method of vaccination thus involves administering to the host several or all of the cloned and purified proteins described above, which are derived from antigenically dissimilar sections of the IP90 cassette string. While a variety of immunogenic compositions may be prepared from such proteins, it is presently preferred that a simple mixture of two or more of the cassette string proteins or peptide fragments thereof be employed for this purpose.

Combinations of the antigen(s) of this invention with other antigens of *B. burgdorferi,* such as the OspA, OspB and OspC proteins, BmpA, B, C or D proteins, or fragments thereof are also encompassed by this invention.

Exemplary carriers are as described above for therapeutic compositions. Optionally, the vaccine composition may further contain adjuvants, preservatives, chemical stabilizers, or other antigenic proteins. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallade, the parabens, ethyl vanillin, glycerin, phenol, and parachlorophenol.

One or more of the above described vaccine components may be admixed or adsorbed with a conventional adjuvant. The adjuvant is used to attract leukocytes or enhance an immune response. Such adjuvants include, among others, Ribi, mineral oil and water, aluminum hydroxide, Amphigen, Avridine, L121/squalene, D-lactide-polylactide/glycoside, pluronic plyois, muramyl dipeptide, killed Bordetella, and saponins, such as Quil A. In addition, a vaccine composition of the invention may further comprise other, non-*B. burgdorferi* antigens, including, *Bordetella bronchiseptica,* canine parvovirus, canine distemper, rabies, Leptosporidia, canine coronavirus, and canine adenovirus. Other vaccinal antigens originating from other species may also be included in these compositions, e.g., feline coronavirus, etc.

The invention thus also encompasses a prophylactic method entailing administering to an animal or human an effective amount of such a composition. The P39.5 and/or cassette string protein antigenic compositions are administered in an "effective amount", that is, an amount of antigen that is effective in a route of administration to provide a vaccinal benefit, i.e., protective immunity. Suitable amounts of the antigen can be determined by one of skill in the art based upon the level of immune response desired. In general, however, the vaccine composition contains between 1 ng to 1000 mg antigen, and more preferably, 0.05 $\mu$g to 1 mg per mL of antigen. Suitable doses of the vaccine composition of the invention can be readily determined by one of skill in the art. Generally, a suitable dose is between 0.1 to 5 mL of the vaccine composition. Further, depending upon the human patient or the animal species being treated, i.e. its weight, age, and general health, the dosage can also be determined readily by one of skill in the art.

In general, the vaccine will be administered once on a seasonal basis. Each tick season, usually in the spring, a booster should be administered. The vaccine may be administered by any suitable route. However, parenteral administration, particularly intramuscular, and subcutaneous, is the preferred route. Also preferred is the oral route of administration. Routes of administration may be combined, if desired, or adjusted.

Further, the vaccine may be a DNA vaccine, which includes the P7-1 DNA sequence or a fragment thereof, another cassette string protein, or a fragment thereof, optionally under the control of regulatory sequences. Thus, the antigen-encoding DNA may be carried in a vector, e.g., a viral vector. Generally, a suitable vector-based treatment contains between $1 \times 10^{-3}$ pfu to $1 \times 10^{12}$ pfu per dose. However, the dose, timing and mode of administration of these compositions may be determined by one of skill in the art. Such factors as the age, and physical condition of the vaccinate may be taken into account in determining the dose, timing and mode of administration of the immunogenic or vaccine composition of the invention.

VIII. Drug Screening and Development

The proteins, antibodies and polynucleotide sequences of the present invention may also be used in the screening and development of chemical compounds or proteins which have utility as therapeutic drugs or vaccines for the treatment or diagnosis or prevention of Lyme Disease. As one example, a compound capable of binding to P39.5 and preventing its biological activity may be a useful drug component for the treatment or prevention of Lyme Disease. The methods described herein may also be applied to fragments of P39.5. Similarly, a compound capable of binding to a cassette string protein, or fragment thereof and preventing its biological activity may be a useful drug component for the treatment or prevention of Lyme Disease.

Suitable assay methods may be readily determined by one of skill in the art. Where desired, and depending on the assay selected, the selected antigen(s), e.g., P39.5, may be immobilized directly or indirectly (e.g., via an anti-P39.5 antibody) on a suitable surface, e.g., in an ELISA format. Such immobilization surfaces are well known. For example, a wettable inert bead may be used. Alternatively, the selected antigen, e.g., P39.5, may be used in screening assays which do not require immobilization, e.g., in the screening of combinatorial libraries. Assays and techniques exist for the screening and development of drugs capable of binding to an antigen of this invention, e.g., P39.5. These include the use of phage display system for expressing the antigenic protein (s), and using a culture of transfected *E. coli* or other microorganism to produce the proteins for binding studies of potential binding compounds. See, for example, the techniques described in G. Cesarini, *FEBS Letters*, 307(1):66–70 (July 1992); H. Gram et al., *J. Immunol. Meth.*, 161:169–176 (1993); C. Summer et al., *Proc. Natl. Acad. Sci. . USA*, 89:3756–3760 (May 1992), incorporated by reference herein.

Other conventional drug screening techniques may be employed using the proteins, antibodies or polynucleotide sequences of this invention. As one example, a method for identifying compounds which specifically bind to a protein of this invention, e.g., P39.5, can include simply the steps of contacting a selected P39.5 protein with a test compound to permit binding of the test compound to P39.5; and determining the amount of test compound, if any, which is bound to the P39.5 protein. Such a method may involve the incubation of the test compound and the P39.5 protein immobilized on a solid support. Similar methods may be employed for one or more of the cassette string proteins.

Typically, the surface containing the immobilized ligand is permitted to come into contact with a solution containing the protein and binding is measured using an appropriate detection system. Suitable detection systems include the streptavidin horse radish peroxidase conjugate, direct conjugation by a tag, e.g., fluorescein. Other systems are well known to those of skill in the art. This invention is not limited by the detection system used.

Another method of identifying compounds which specifically bind to P39.5 or another protein of this invention can include the steps of contacting the protein, e.g., P39.5, immobilized on a solid support with both a test compound and the protein sequence which is a receptor for P39.5 to permit binding of the receptor to the P39.5 protein; and determining the amount of the receptor which is bound to the P39.5 protein. The inhibition of binding of the normal protein by the test compound thereby indicates binding of the test compound to the P39.5 protein. Similar methods may be employed for one or more of the cassette string proteins.

Thus, through use of such methods, the present invention is anticipated to provide compounds capable of interacting with P39.5 or portions thereof, and/or the cassette string protein(s) or portions thereof and either enhancing or decreasing the protein's biological activity, as desired. Such compounds are believed to be encompassed by this invention. Further wherever, above or below, the P39.5 protein is mentioned, it may be substituted with P7-1 or one or more of the other cassette string proteins.

The following examples illustrate the preferred methods for obtaining protein antigens of the invention and preparing the assays and compositions of the invention. Significantly, these examples indicate that the P39.5 antigen of this invention is useful for diagnosis and prophylaxis against Lyme disease and may improve Lyme serology. These examples are illustrative only and do not limit the scope of the invention.

EXAMPLE 1

Borrelia Bacterial Strains and Antibodies

A. Bacterial Strains

The JD1 strain of *B. burgdorferi* sensu stricto [J. Piesman et al., *J. Clin. Microbiol.*, 25:557–558 (1987) and T. G. Schwan et al, *J. Clin. Microbiol.*, 27:1734–1738 (1989)] was obtained from the Center for Disease Control and Prevention and kept in frozen stocks of low passage (<7). B31 is also a strain of *B. burgdorferi* sensu stricto obtained from the CDC and kept as above. IP90 is a strain of *B. garinii* which was also furnished by the CDC.

*B. burgdorferi* organisms were cultured at 34° C. in a BSK-H culture medium (Sigma Chemical Co., St. Louis, Mo.).

B. Monkey Antibodies

Live spirochetes were incubated with serum antibody from rhesus monkeys that had been infected with *B. burgdorferi* strain JD1 by the bite of *I. scapularis* nymphs. Unbound antibodies were washed off the spirochetes and bound antibodies were removed with a low pH buffer. Monkey antibodies were obtained from three sources:

a) from rhesus monkeys infected with *B. burgdorferi* strain JD1 by needle inoculation, b) from rhesus monkeys infected with *B. burgdorferi* strain JD1 by exposure of the animals to JD1-infected nymphs of *Ixodes scapularis*, c) by affinity purification on live spirochetes using as starting material antiserum that was collected from tick-inoculated animals, as follows: A volume of 800 µl of diluted (1/40 in BSK-H medium), heat-inactivated serum samples pooled from 3 tick-inoculated animals are incubated with 1×10⁹ total live bacteria at room temperature for 30 minutes. After the incubation, the samples were centrifuged at 13,000×g for 15 minutes at 4° C. The supernatant was then readsorbed two more times as described above. The bacterial pellet that was recovered after the first adsorption was washed three times with BSK-H to remove unbound antibodies. After the last wash, the pellet was resuspended in 400–500 µl of 0.2 M glycine-HCl, pH 2.2, 0.5 M NaCl, and centrifuged. The supernatant was recovered and the pH brought to 7.00 by the addition of 2.0 M Tris base.

EXAMPLE 2

Preliminary Identification of P39.5 of IP90

The antibodies of Example 1, section B were reacted with Western blots of whole extracts from JD1, B31 and IP90 spirochetes. Western blots were performed as follows: Antigen preparations were electrophoresed in 15% acrylamide mini gels (10×10×0.1 cm) with a 5% acrylamide stacking gel. Twenty µl of lysate containing 7×10⁸ solubilized bacteria or 25 µg of protein (measured by OD at 280 nm) were dispensed per track (the whole preparative track is equal to 16 single tracks; therefore 400 µg protein were loaded onto each preparative gel). Electrophoresis was performed using a mini-gel apparatus (Integrated Separation Systems, Hyde Park, Mass.) at a constant current of 23 mA, with the buffers of U. Laemmli, Nature, 227:680–685 (1970). For immunoblotting, the proteins from the polyacrylamide gels were electrotransferred to nitrocellulose paper (Schleicher and Schuell, Keene, N.H.) overnight at a constant voltage of 22 V in a Mighty Small transfer unit (Hoeffer Scientific Instruments, San Francisco, Calif.) as described by H. Towbin et al, Proc. Natl. Acad. Sci. USA, 76:4350–4354 (1979). Efficiency of transfer was assessed by staining part of the nitrocellulose with colloidal gold (Integrated Separation Systems). Nitrocellulose membranes were blocked with 3% fat-free powdered milk (Carnation) prepared in PBS containing 0.05% Tween-20 (Integrated Separation Systems) (PBS-T) for two hours at room temperature.

After the blocking step, the membranes were mounted in a Miniblotter 45 (Immunetics, Cambridge, Mass.) according to the manufacturer's instructions, and 110 µl of each serum sample diluted 1/50 with PBS-T were introduced into the Miniblotter's channels and allowed to interact with the nitrocellulose membrane for 1 hour at room temperature on a rocking platform. After the incubation, the manifold system was used to wash the membranes with PBS-T. At this point the Miniblotter was disassembled and the blot was taken out. The rest of the incubation steps were performed in small trays. After the wash, the membranes were incubated for 1 hour with biotinylated anti-human IgM (µ-chain-specific) and IgG (γ-chain-specific) antibodies (Vector Laboratories, Burlingame, Calif.) diluted 1/200 in PBS-T. Biotinylated antibodies were probed with an avidin/biotinylated horseradish peroxidase complex (Vector) prepared according to the manufacturer's instructions. The reagent 4-chloro-1-naphthol (Sigma) was used as a chromogen. The color reaction was stopped by washing the membranes with distilled water.

A Western blot (FIG. 6) was prepared of lysates from spirochetes of B. burgdorferi strains JD1 and B31 and B. garinii strain IP 90 developed with serum from monkeys needle-inoculated and tick-inoculated with the JD1 spirochetes, and antibodies from the latter serum affinity purified off of whole live JD1 spirochetes. The affinity purified antibody recognized four antigens on Western blots of whole lysates from spirochetes of B. burgdorferi JD1. The antigens were named P1 (Relative molecular mass (Mr) 39–40,000), P2 (Mr 35–37,000), P3 (Mr 22–24,000) and P4 (Mr 18–19,000). These antigens were also recognized, as expected, by serum samples from needle-inoculated animals and by serum from tick-inoculated monkeys. In addition, this Western blot indicated that the affinity-purified antibodies recognized what appeared to be P1, P2, and P4 on B31 spirochetes and what appeared to be P1 (but with a slightly higher relative molecular mass) in B. garinii as well as an additional antigen of higher relative molecular mass. These two latter antigens were also exclusively recognized by the sera from both needle- and tick-inoculated animals. P1 was eventually identified as P39, also known as BmpA. The similar antigen present on IP90 spirochetes was tentatively identified as P39.5 and was shown on the Western blot discussed above.

EXAMPLE 3

Antibody-dependent Complement-mediated Killing of JD1, B31 and IP90 Spirochetes

Serum from tick-inoculated monkeys was employed in an ADCK assay as follows. Frozen samples of B. burgdorferi are quickly thawed at 37° C., cultured until they have reached mid-log phase (approximately 3 days, 1–2×10⁷ spirochetes/ml), centrifuged at 8,000×g for 20 minutes, resuspended in BSK-H medium, and counted. The ADCK assay was carried out in duplicate in 96-well tissue culture plates (Costar). A total of 5–6×10⁵ spirochetes in 25 µl of BSK-H medium was added to each well containing 50 µl of heat-inactivated (56° C., 30 minutes) serum samples diluted to 1:10 in the same medium. The plates were incubated at 34° C. under a gas mixture of 3% $CO_2$, 5% $O_2$ and the balance of $N_2$ for 20 minutes before the addition of 25 µl of complement (normal monkey serum). After 18–24 hours of incubation under the same conditions, the total numbers of dead (nonmotile) and live (motile) bacteria were quantified under a dark-field microscope. Equivalence between non-motility and death in a similar assay has been determined before [M. Aydintug et al., cited above]. Killing was considered significant if the mean % of dead spirochetes exceeds three times the value of the mean % killing observed in the presence of normal serum.

Figure 1:
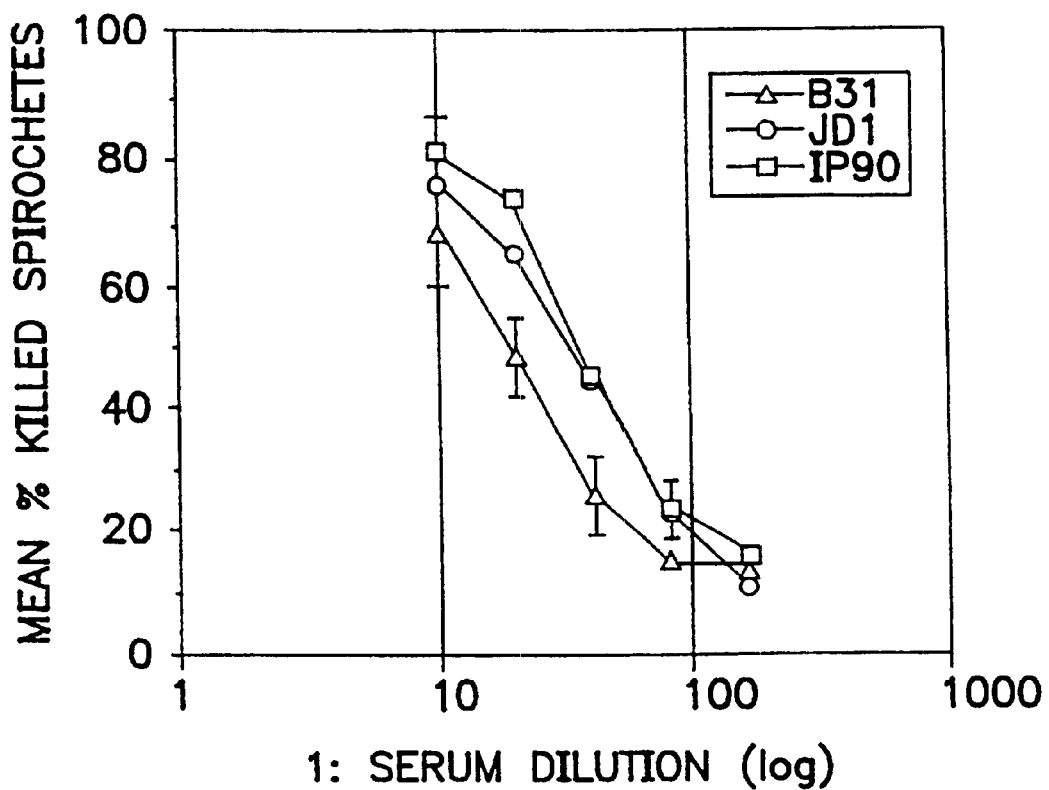
FIG. 1 is a graph of the antibody dependent, complement-mediated killing (ADCK) titration of spirochetes from *B.* burgdorferi strains JD1 (○), B31 (Δ), and *B. garinii* strain IP90 (□) with serum from a rhesus monkey tick-inoculated with JD1 spirochetes.

ADCK was performed with spirochetes from B. burgdorferi strains JD1 and B31 and B. garinii strain IP90, using serum from animals that were tick inoculated with JD1 spirochetes. As shown in Example 2, this serum recognized only two antigens on IP90 blots, one of a relative molecular mass similar to that of P1, and one of higher relative molecular mass. As is shown in FIG. 1, all three spirochetal strains were killed by the serum, indicating that at least one of the antigens shown in the IP90 Western blot was the target of ADCK.

EXAMPLE 4

Identification of P39.5

The identity of the putative BmpA (P39) band seen on the IP90 Western blots was investigated. A Western blot of lysates from JD1 and IP90 was developed with anti-flagellin monoclonal antibody (Mab); anti-P39 Mab; anti-P39 polyclonal antibody; anti-P35 Mab; anti BmpD polyclonal; and sera from two monkeys tick-inoculated with JD1 spirochetes. In the comparative Western blot analysis of JD1 and IP90 antigens that were run on the same gel, both antigen extracts reacted with the anti-flagellin Mab H9724. However, an anti-BmpA Mab reacted only with JD1 BmpA, and serum from the monkey immunized with recombinant BmpA from JD1 reacted strongly with the JD1 blot, as expected, but very faintly with the BmpA antigen from IP90. Moreover, serum samples obtained from two JD1-infected monkeys reacted with the same two antigens as before on the IP90 blot and occasionally yielded additional (more faint) bands of higher molecular mass. The band of lowest molecular mass of the two corresponds in fact to a larger molecule than the BmpA from IP90, as identified with the anti-BmpA polyclonal antibody. The higher molecular mass band likely corresponds to flagellin, as it had the same molecular mass as the band of IP-90 that reacted with the MAb H9724.

A monoclonal antibody raised against P35 from JD1 reacted with this molecule on the JD1 blot but not on the IP90 blot, whereas a mouse polyclonal antiserum raised against JD1 BmpD reacted with BmpD of both JD 1 and IP90, although the BmpD band of IP90 was very faint. Thus, the identity of the IP90 antigen that could be the target of the ADCK was not BmpA, BmpD or P35. It was referred to hereafter as P39.5.

A Western blot was then developed of lysates of JD1 and IP90 spirochetes incubated with serum from a monkey tick-inoculated with JD1; monkey polyclonal antiserum to P39; mouse Mab H9724 to flagellin; monkey anti-P39.5 antibody obtained by affinity purification from a serum sample from a monkey tick-inoculated with JD1; and mouse anti-recombinant P7–1 (rP7–1). To identify P39.5 on Western blots of JD1 lysates, the anti-P39.5 antibody elicited in JD1-infected monkeys was affinity purified using nitrocellulose strips that had P39.5 from IP90 attached to them. As expected, this antibody reacted with the P39.5 antigen on a Western blot of IP90 lysate but, surprisingly, failed to react with the JD1 blot. This result implied that P39.5 of JD1 was either not expressed in vitro, was sparsely expressed as to be undetectable by the affinity-purified anti-P39.5 antibody on the JD1 blots, or was expressed in vitro by JD1 in a manner that was not cross-reactive antigenically with the antibody affinity purified off of the P39.5 of IP90.

Obviously, JD1 spirochetes had to express P39.5 in vivo and in amounts sufficiently high as to be immunogenic, since otherwise the anti-P39.5 antibody that was affinity purified would not have been elicited in the first place. In the above described Western blot, the position of BmpA was indicated by its reaction with the anti-BmpA polyclonal antiserum and that of flagellin by the reaction of this molecule with Mab H9724.

A new Borrelia antigen that is abundantly expressed in vitro by the *B. garinii* strain IP90 and in vivo by the *B. burgdorferi* sensu stricto strain JD1 was thus identified. This antigen, P39.5, was the target in the ADCK of IP90 spirochetes.

EXAMPLE 5

Cloning of P39.5

A. Cloning in bacteriophage

A library of randomly-sheared total DNA from *B. garinii* IP90 was constructed in the λZAPII bacteriophage vector [Stratagene, La Jolla, Calif.] and screened with a pool of plasma collected from rhesus monkeys infected with the JD1 strain of *B. burgdorferi*. The plasma samples used for the pool were selected such that they contained antibody that recognized only P39.5, the putative flagellin and the 1 or 2 additional unidentified higher molecular mass faint bands seen on some IP90 Western blots.

After several rounds of screening, eleven clones were rescued into the pBluescript phagemid [Stratogene] the recombinant plasmids were purified and used to transform cells of the SURE strain of *E. coli*. Several transformants were selected from each original clone, the presence of the insert was confirmed, and one such transformant from each clone was grown, induced for expression, lysed and analyzed by Western blot with the original plasma pool. The eleven cloned fragments hybridized to each other by dot-blot hybridization.

One of the eleven clones (named 7-1) was selected for over-expression and purification on the basis of the strong reactivity of the expressed protein with the plasma antibodies. The 7-1 insert was 950 bp in length.

The identity of the expressed protein was confirmed as antigenically identical to, or cross-reactive with, P39.5, by showing that antibody from the original plasma sample that was affinity purified using the clone as immunoabsorbant reacted with P39.5 on a Western blot of *B. garinii* lysate. A Western blot was developed of lysates from IP90 spirochetes reacted with plasma from a monkey infected with JD1 spirochetes; antibody from the same plasma affinity purified with the recombinant antigens as expressed by *B. garinii* clone 1-1 and clone 7-1. Reactivity of the IP90 lysate with the monkey plasma pool was demonstrated in the blot. Reactivity of the IP90 lysate with the antibody affinity purified with the recombinant 1-1 protein was shown, and with the antibody affinity purified with the recombinant 7-1 protein.

A partial DNA sequence for P7-1 was obtained [SEQ ID NO: 1]. About 950 bp were derived from clone 7-1. In addition, about 140 kb of the upstream regions were obtained from clone 14 [SEQ ID NO: 13]. The DNA fragment formed by the 5' SEQ ID NO: 13 sequence and the SEQ ID NO: 1 sequence is 1189 bp in length, which is depicted in FIG. 2. It encompasses a single open reading frame which encodes a deduced protein of 37.7 kDa. Its high alanine content results in this rather low molecular mass. Since the average molecular mass of this protein's amino acids is 95, there are about 57 bp of the complete coding region missing. Since no hydrophobic leader sequence was observed and since P39.5 has the solubility properties of lipoproteins (see below), it follows that P7-1 is antigenically cross-reactive with P39.5, but is not the complete P39.5 itself Data other than the deduced amino acid sequence of P7-1 [SEQ ID NOS: 14 and 2] suggests that P39.5 is a lipoprotein. First, the native form of P39.5 present in whole-cell extracts of IP90 spirochetes was fully extractable, i.e., partitions into, the detergent phase in a Triton-X114 phase separation experiment. Second, most of its sequence is composed of hydrophilic domains, very much like OspA, yet it must be expressed on the outer surface, since it is targeted by antibody. Third, its % identity with several members of the Vmp family of *Borrelia hermsii* lipoproteins is considerable, e.g., 22% with Vmp4, 19% with Vmp23, 18% with Vmp 17, and 17% with Vmp21. These sequences are available on the GENBANK database.

An interesting feature of its nucleotide sequence is the presence of several internally repeated regions, shown in FIG. 2. Blocks IA and IB are 70% identical. Block IIA is as much as 91% identical to IIB, and blocks A, B and C are between 84 and 90% identical. The only internally unique fragment is that denoted by the black block. Clearly, such a molecule will be prone to undergoing homologous recombinations of the same kind that occur between and within the OspA and OspB genes, which have regions of homology [P. Rosa et al, cited above]. However, such potential escape mutants may not escape the combined action of antibody and complement, as demonstrated by reference to the case of OspA [Sole et al, cited above].

B. Expression and purification of recombinant P7–1 with the QIAEXPRESS™ System

The Qiaexpress™ system from Qiagen, Inc. (Chatsworth, Calif.) takes advantage of the high affinity of six consecutive histidine residues for divalent cations such as Ni. The latter is conjugated to nitrilo-tri-acetic acid (NTA), which in turn is linked to agarose. Since the affinity tag is very small (minimally 6 residues) it may be left in the fusion protein without serious consequences with regard to the protein antigenic properties. The 6×His affinity tag may be incorporated either at the N- or C-terminus. A range of vectors (pQE vectors) are available for constructing both types of fusion.

Recombinants were initially screened for the presence of expected inserts in the plasmids. This was followed by a Western blot to confirm protein expression in these recombinants. Westerns blots were developed either with serum from control mice infected with the spirochetes of the corresponding strain or with a mouse antibody that specifically detects the MRGS(His)6 epitope (Qiagen), which was the affinity tag sequence present in some of the pQE vectors [for N-terminal fusions]. An equally sensitive alternative was to use Ni-NTA-alkaline phosphatase conjugate, which was also available from Qiagen.

The $E.$ $coli$ cells containing the fusion construct were grown to mid-log phase, induced with 0.3 mM IPTG for a period of three hours, pelleted, washed once with Sonication buffer [50 mM $NapO_4$, pH 8.0, 300 mM NaCl] and stored overnight at $-20°$ C. On the next day, cells were resuspended in Sonication buffer and sonicated on ice using 15-second pulses for a total of 2 minutes. Immediately following sonication the serine protease inhibitor PMSF (phenyl-methyl-sulfonide fluoride) was added to prevent degradation by such proteases. The cell debris was spun down, and the supernatant transferred to a fresh tube. In the mean time, the Ni-NTA resin was washed once with 10 column volumes (cv) of the Sonication buffer. The fusion protein was allowed to bind to the Ni-NTA resin in a tube for 1 hour. The resin was spun down and the supernatant discarded. The resin was resuspended in 10 cv of Sonication buffer, poured into a column and washed 3 times with 10 cv of the same buffer followed by 3 10-cv washes with Wash buffer [50 mM $NapO_4$, pH 6.3, 300 mM NaCl]. Finally, the fusion protein was eluted with 10 cv of Elution buffer [50 mM $NapO_4$, pH 4.5, 300 mM NaCl] and fractions collected. Fractions were assayed for protein and the fractions that contain the highest protein concentration pooled and neutralized to pH 7.0 with dibasic $NapO_4$. The protein concentration in the pooled sample was calculated and an aliquot run on a SDS-PA gel and stained with silver to check purity. Typical yields were about 4–5 mg/liter of culture.

EXAMPLE 6

In Vitro Protective Potential of P7-1 in Monkeys

Anti-P7-1 antibody was purified from the same monkey plasma pool used to screen the DNA library, by absorbing and acid-eluting it off of nitrocellulose strips that contained the recombinant P7-1 protein (rP7-1) as expressed from clone 7-1. The monospecificity of the antibody was confirmed on a Western blot as described in Examples 2 and 4, and the antibody was used in ADCK as described in Example 3.

The fraction of dead IP90 spirochetes after a 24 hour incubation with the affinity purified anti-p7-1 antibody was 55% (FIG. 3, bar 2). The antibody was reconstituted at a concentration equivalent to a 1:10 dilution of its concentration in plasma. This killing rate was comparable to that observed with a 1:10 dilution of the same plasma (67%, FIG. 3, bar 1). Complement was essential to effect killing, as only 12% of the spirochetes was killed in its absence (FIG. 3, bar 3). Killing in the presence of monkey complement alone was slightly higher than usual, in that the value was 25% (FIG. 3, bar 4) whereas the value most frequently obtained was 10–15%, albeit with JD1 spirochetes [M. Aydintug el al, $Infect.$ $Immun.,$ 62:4929–4937 (1994)]. In BSK-H medium alone 12% of the spirochetes died (bar 5).

These results indicated that antibody to the recombinant P7–1 (a fragment of P39.5) antigen of IP90, elicited in monkeys during the course of a natural infection with JD1 spirochetes, could kill IP90 spirochetes by ADCK.

These experiments demonstrated the protective potential of P7–1 and formed the basis of selection of this antigen as a vaccine candidate.

EXAMPLE 7

Protective Potential of P7-1 in Mice

This example shows that mice may be directly immunized with the recombinant P7-1. The mouse antibodies generated by immunization with rp7-1 and Ribi adjuvant were able to kill up to 60% of IP90 spirochetes in vitro, by antibody-dependent, complement-mediated killing (ADCK). To assess the protective potential of P7-1 more directly, the DNA fragment of clone 7-1 was subcloned in the pQE as described in Example 5, and the expressed protein was purified in milligram quantities and used to immunize C3H/HeJ mice. Mice were given four injections of 30 $\mu$g each of the recombinant P7-1in 0.2 ml of Ribi R-700 adjuvant (Ribi ImmunoChem Research, Inc., Hamilton, Mont.). The R-700 formulation of 0.25 mg/ml MPL™, 0.25 mg/ml synthetic trehalose dicorynomycolate, 20 $\mu$l/ml Squalene (hexamethyl-tetracosahexane) and 2 $\mu$l/ml monooleate (Tween 80). Injections were given intraperitoneally, three weeks apart. Two weeks after the last immunization, mice were bled, specificity of the elicited antibody was confirmed by Western blot using whole cell extracts of IP90 spirochetes as antigen, and serum samples were pooled.

Serum from mice immunized with the Ribi adjuvant alone recognized no antigens on IP90 blots. Serum from mice immunized with rP7-1 and Ribi recognized, as expected, the P39.5 band on IP90 lysates, but also a weaker band slightly above the 41 kdDa flagellin band, and a higher molecular mass band as well. Interestingly, this same mouse antibody recognized a 41 kDa band on Western blots of JD1 lysates, and also a slightly higher molecular mass antigen.

This result differed from that obtained with affinity-purified anti-rP7-1 antibody from monkeys in the preceding example and was probably due to the fact that the mouse antibody's affinity was allowed to mature for much longer (12 weeks) than that of the monkey antibody (4–5 weeks). As a consequence, its binding affinity was higher but its specificity was lower and it can bind to crossreactive but nonidentical epitopes.

After an additional booster injection, the mice that yielded the anti-P7-1 antibody that killed 60% of IP90 spirochetes by ADCK in vitro yielded an antiserum that killed 100% of such spirochetes in an experiment of the same kind. In addition, this same antiserum was able to kill 50% of spirochetes from strain NT1 (a strain as yet untyped but probably sense stricto, as it was isolated from the cerebrospinal fluid of a patient in the North East of the United States). In contrast, no spirochetes of the JD1 strain could be killed either in vitro (by ADCK) or in vivo, in a tick-challenge experiment with mice immunized with rP7-1 and Ribi adjuvant.

ADCK was assessed both with monkey and with guinea pig complement. Normal guinea pig serum (from Sigma Chemical Co., St. Louis, Mo.) was used as a source of complement in the latter case. The same monkey plasma pool from animals infected with B. burgdorferi JD1 was used as a positive control. At a dilution of 1:10, this plasma pool killed 57% of IP90 spirochetes after a 24 hour incubation (FIG. 3, bar 1). Mouse antiserum to the rP39.5 killed 73.5% of the spirochetes at a dilution of 1:10 and 60.5% at 1:50 (bars 2 and 3, respectively). Serum from mice immunized with Ribi adjuvant alone killed 21% of the spirochetes (bar 4). Guinea pig complement was less effective in the ADCK assay. A fraction of 37% of the spirochetes was killed with the positive control plasma at 1:10 (bar 5) whereas the mouse anti-P39.5 antiserum at the same dilution killed 48% of the spirochetes in the presence of Guinea pig complement (bar 6). A fraction of 12% of the spirochetes was killed in the presence of a 1:10 dilution of serum from mice given Ribi alone (bar 7). Interestingly, only 6% of JD1 spirochetes were killed when incubated with a 1:10 dilution of the mouse anti-r39.5 antiserum, a fraction that did not differ from that killed with just control serum (not shown). Hence, the bands recognized on the JD1 blot probably represent a spurious crossreactivity, but not the JD1 P39.5.

EXAMPLE 8

Diagnostic Use of P7-1 in Humans

Nineteen human serum samples were obtained from the Centers for Disease Control and Prevention (CDC). Four of these samples were from donors who had no history of Lyme disease and had never resided in an area where this disease is endemic. The other fifteen samples were from patients who lived in Lyme disease endemic areas, had signs and/or symptoms of the disease, and, with the exception of one patient, were serologically positive by the criterion recommended by the CDC. That criterion provides that patients be positive by a sensitive Lyme ELISA test and be also positive by either an IgM or an IgG Western blot, such that at least two of the following three bands were present in positive IgM blots (24, 39, or 41 kDa) and five of the following ten bands were present in positive IgG blots (18, 21, 28, 30, 39, 41, 45, 58, 66, and 93 kDa).

The test, based on detection of IgG antibody by incubating serum samples diluted at 1:200 with nitrocellulose strips onto which purified P39.5 antigen had been electroblotted, and subsequent detection of bound antibody by the immunoenzymatic methods described in Example 2, yielded the following results. The four serum samples from donors who had no history of Lyme disease and had never resided in an area where this disease is endemic had no detectable anti-P39.5 antibody. Of the fifteen remaining samples, fourteen were positive. The only negative sample was that which also had failed to show antibody by the criterion recommended by the CDC. Thus, the simple procedure described herein based on the P39.5 antigen as a diagnostic probe for anti-B. burgdorferi antibody is, by this initial assessment, as sensitive and specific as the more complex two-step method that is currently recommended by the CDC.

In another diagnostic assay, the antigenic protein expressed from the 7-1 DNA fragment, rP7-1, was tested as a probe for the early serological diagnosis of Lyme disease in rhesus monkeys. Serum samples obtained from three pairs of rhesus monkeys infected with three different strains of B. burgdorferi, B31, JD1 and NT1, respectively, contained detectable antibody to purified rP7-1 by week 2 of infection, as detected by Western blot. Both IgM and IgG antibodies were tested simultaneously. The result indicates that antibody to P7-1 appears early in the course of infection, regardless of the strain of B. burgdorferi that is eliciting the antibody response.

The sensitivity of antibody detection was assessed again by Western blot as above, with a battery of 43 human serum samples obtained from the CDC. The experiment was performed in a blinded fashion. The CDC samples had been obtained from patients with a clinical diagnosis of Lyme disease that satisfied the stringent CDC criteria for case definition. Of the 43 samples from clinically positive patients, 34 were reported positive by the CDC, as judged by the Dressier criteria [Dressler, F. et al, 1993 J. Infect. Dis., 167:392–40] using the Western blot test from MarDx Diagnostics. Inc. (Lyme disease MarBlot). With the diagnostic Western blot based on the P7-1 antigen, an equal number of samples were positive (34), although negative or positive results did not always coincide in both assays. Thus, the P7-1-based Western, in which a single band is (or is not) detected and which is therefore a test simple to interpret, yielded the same sensitivity as one of the most accomplished, yet cumbersome to interpret, Lyme disease diagnostic tests presently in the market.

In tests for antigenic specificity, so far, from 12 serum samples of syphilitic patients, 11 were negative with the assay despite the fact that all of the samples contained antibodies that cross-reacted with multiple antigens on a Western blot of whole B. burgdorferi antigens. The single serum sample that gave a positive result was from a patient who also had an HIV infection and several AIDS-related infections.

EXAMPLE 9

The Cassette String Proteins

As stated above, the amino acid sequence predicted from the nucleotide sequence of the 7-1 fragment is about 50% identical to the VlsE of the B31 strain of B. burgdorferi, which is part of an antigen of B. burgdorferi that undergoes antigenic variation by a mechanism of recombination whereby a central fragment of the expressed copy (VlsE) is recombined with fragments from a string of 15 "cassettes" located upstream from the expressed copy [J. Zhang, cited above].

Several DNA fragments have been cloned which appear to be part of the cassette string of B. garinii IP90. In addition to 7-1, these fragments, named 1-1, 3-1, 6-1, 9-1, and 12-1 are between 1 and 2 kb in length. When expressed in recombinant form, substantially as described above for P7-1 (off of the lacZ promoter of pBluescript), each of the cassette string fragments expresses a peptide which is commensurate with the size of the insert and which reacts with antibody from infected monkeys. None of the 5' ends of these fragments contains a hydrophobic leader or a signal peptidase II consensus sequence of the type that is characteristic of bacterial lipoproteins. These fragments must therefore be part of the cassette string of IP90 and, like the cassette string of B31, they are in-frame. DNA sequences of the 5' and 3' termini (between about 100–500 bp) of each fragment are illustrated in SEQ ID NOS: 3 through 12. Note that only the 5' end of fragment 9–1 is illustrated in SEQ ID NO: 10.

The antigenicity of these fragments has been analyzed in two ways. First, the reactivity of the fragments' Western blots with serum samples collected longitudinally from rhesus monkeys was studied over a period of 48 weeks after a tick inoculation with *B. burgdorferi* JD1. Proteins expressed by fragments 9-1 and 7-1 reacted predominantly with serum samples collected between weeks 2 and 24 post-infection infection (PI) (early reactors), proteins expressed by fragments 3-1 and 6-1 reacted chiefly with serum samples collected between weeks 24 and 48 PI (late reactors), and proteins from fragments 1-1 and 12-1 showed a largely uniform reactivity over the 48-week-long time span investigated. This result suggests that each of the cloned fragments contains unique epitopes.

To confirm this notion, a serum pool was constructed with the samples employed in the Western blot analysis described above, and an aliquot of this "time" pool was pre-incubated with an excess of the purified antigen expressed from 7-1 (rP7-1). In this way, the anti-P7-1 antibody that was present in the serum pool was no longer available to react with the P7-1 antigen on Western blots. Nonetheless, this serum pool was still able to react with the proteins expressed from the other DNA fragments, with the exception of 12-1. Since the latter is a "late" reactor, it is possible that antibodies to the putatively unique epitopes of 12-1 may have been diluted out in the serum pool. All of the above fragment were subcloned into the pQE vector for expression using conventional methodologies, as described above for P7-1.

The inventor has theorized that the mechanism of antigenic variation to which the IP90 P39.5 antigen is subjected, by virtue of its homology to the vls E antigens of B31, indicates that this antigen is crucially important for spirochetal survival in the vertebrate host. Thus, the methods and compositions of this invention are designed to circumvent this spirochetal defense mechanism by immunizing a host with a large fraction of the epitopes that are expressed on the cassette string that is the very source of the variation. This is made possible by the unique fact that most of this cassette string is in frame. Therefore, as mentioned above, one method of vaccination involves administering to the host several or all of the cloned and purified proteins described above, which are derived from antigenically dissimilar sections of the IP90 cassette string. See, e.g., the results obtained when P7-1 was introduced into a host and induced antibodies which killed the spirochetes.

All above-noted references and priority document are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A recombinant or synthetic protein or peptide that binds with antibodies to the causative agent of Lyme Disease in infected humans or animals, said protein or peptide selected from the group consisting of:
   (a) an amino acid sequence of SEQ ID NO: 2;
   (b) an amino acid sequence of SEQ ID NO: 14;
   (c) an amino acid sequence encoded by SEQ ID NO: 3;
   (d) an amino acid sequence encoded by SEQ ID NO: 7;
   (e) an amino acid sequence encoded by SEQ ID NO: 11; and
   (f) an amino acid sequence of a fragment of (a) through (e) of at least five amino acids in length.

2. The protein or peptide according to claim 1, wherein said fragment is at least eight amino acids in length.

3. The protein or peptide according to claim 1, wherein said peptide or protein is coupled to a substrate that immobilizes said peptide or protein.

4. The protein or peptide according to claim 1, wherein said peptide or protein is coupled to a detectable label or signal generating reagent.

5. A kit for diagnosing infection with a causative agent of Lyme Disease in a human or animal comprising a protein or peptide of claim 1.

6. The kit according to claim 5, further comprising at least one of the group consisting of a substrate that immobilizes said peptide or protein, a detectable label, a labeled conjugate, and a signal generating reagent.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 1047 base pairs
      (B) TYPE: nucleic acid
      (C) STRANDEDNESS: double
      (D) TOPOLOGY: unknown (ii) MOLECULE TYPE: cDNA (ix) FEATURE:
      (A) NAME/KEY: CDS
      (B) LOCATION: 1..1047

(xi) SEQUENCE DESCRIPTION: SEQ ID NO: 1:

```
AAG AAT AAT GAT CAT GAT AAT CAT AAG GGG ACT GTT AAG AAT GCT GTT      48
Lys Asn Asn Asp His Asp Asn His Lys Gly Thr Val Lys Asn Ala Val
  1               5                  10                  15

GAT ATG GCA AAG GCC GCT GAG GAA GCT GCA AGT GCT GCA AGT GCT GCT      96
Asp Met Ala Lys Ala Ala Glu Glu Ala Ala Ser Ala Ala Ser Ala Ala
             20                  25                  30

ACT GGT AAT GCA GCG ATT GGG GAT GTT GTT AAG AAT AGT GGG GCA GCA     144
Thr Gly Asn Ala Ala Ile Gly Asp Val Val Lys Asn Ser Gly Ala Ala
         35                  40                  45

GCA AAA GGT GGT GAG GCG GCG AGT GTT AAT GGG ATT GCT AAG GGG ATA     192
Ala Lys Gly Gly Glu Ala Ala Ser Val Asn Gly Ile Ala Lys Gly Ile
     50                  55                  60

AAG GGG ATT GTT GAT GCT GCT GGA AAG GCT GAT GCG AAG GAA GGG AAG     240
```

```
Lys Gly Ile Val Asp Ala Ala Gly Lys Ala Asp Ala Lys Glu Gly Lys
 65                  70                  75                  80

TTG GAT GCT ACT GGT GCT GAG GGT ACG ACT AAC GTG AAT GCT GGG AAG       288
Leu Asp Ala Thr Gly Ala Glu Gly Thr Thr Asn Val Asn Ala Gly Lys
                     85                  90                  95

TTG TTT GTG AAG AGG GCG GCT GAT GAT GGT GGT GAT GCA GAT GAT GCT       336
Leu Phe Val Lys Arg Ala Ala Asp Asp Gly Gly Asp Ala Asp Asp Ala
            100                 105                 110

GGG AAG GCT GCT GCT GCG GTT GCT GCA AGT GCT GCT ACT GGT AAT GCA       384
Gly Lys Ala Ala Ala Ala Val Ala Ala Ser Ala Ala Thr Gly Asn Ala
        115                 120                 125

GCG ATT GGA GAT GTT GTT AAT GGT GAT GTG GCA AAA GCA AAA GGT GGT       432
Ala Ile Gly Asp Val Val Asn Gly Asp Val Ala Lys Ala Lys Gly Gly
    130                 135                 140

GAT GCG GCG AGT GTT AAT GGG ATT GCT AAG GGT ATA AAG GGG ATT GTT       480
Asp Ala Ala Ser Val Asn Gly Ile Ala Lys Gly Ile Lys Gly Ile Val
145                 150                 155                 160

GAT GCT GCT GAG AAG GCT GAT GCG AAG GAA GGG AAG TTG AAT GCT GCT       528
Asp Ala Ala Glu Lys Ala Asp Ala Lys Glu Gly Lys Leu Asn Ala Ala
                165                 170                 175

GGT GCT GAG GGT ACG ACT AAC GCG GAT GCT GGG AAG TTG TTT GTG AAG       576
Gly Ala Glu Gly Thr Thr Asn Ala Asp Ala Gly Lys Leu Phe Val Lys
            180                 185                 190

AAT GCT GGT AAT GTG GGT GGT GAA GCA GGT GAT GCT GGG AAG GCT GCT       624
Asn Ala Gly Asn Val Gly Gly Glu Ala Gly Asp Ala Gly Lys Ala Ala
        195                 200                 205

GCT GCG GTT GCT GCT GTT AGT GGG GAG CAG ATA TTA AAA GCG ATT GTT       672
Ala Ala Val Ala Ala Val Ser Gly Glu Gln Ile Leu Lys Ala Ile Val
    210                 215                 220

CAT GCT GCT AAG GAT GGT GGT GAG AAG CAG GGT AAG AAG GCT GCG GAT       720
His Ala Ala Lys Asp Gly Gly Glu Lys Gln Gly Lys Lys Ala Ala Asp
225                 230                 235                 240

CGT ACA AAT CCC ATT GAC GCG GCT ATT GGG GGT GCG GGT GAT AAT GAT       768
Arg Thr Asn Pro Ile Asp Ala Ala Ile Gly Gly Ala Gly Asp Asn Asp
                245                 250                 255

GCT GCT GCG GCG TTT GCT ACT ATG AAG AAG GAT GAT CAG ATT GCT GCT       816
Ala Ala Ala Ala Phe Ala Thr Met Lys Lys Asp Asp Gln Ile Ala Ala
            260                 265                 270

GCT ATG GTT CTG AGG GGA ATG GCT AAG GAT GGG CAA TTT GCT TTG AAG       864
Ala Met Val Leu Arg Gly Met Ala Lys Asp Gly Gln Phe Ala Leu Lys
        275                 280                 285

GAT GCT GCT GCT GCT CAT GAA GGG ACT GTT AAG AAT GCT GTT GAT ATA       912
Asp Ala Ala Ala Ala His Glu Gly Thr Val Lys Asn Ala Val Asp Ile
    290                 295                 300

ATA AAG GCT GCT GCG GAA GCT GCA AGT GCT GCA AGT GCT GCT ACT GGT       960
Ile Lys Ala Ala Ala Glu Ala Ala Ser Ala Ala Ser Ala Ala Thr Gly
305                 310                 315                 320

AGT GCA GCA ATT GGG GAT GTT GTT AAT GGT AAT GGA GCA ACA GCA AAA      1008
Ser Ala Ala Ile Gly Asp Val Val Asn Gly Asn Gly Ala Thr Ala Lys
                325                 330                 335

GGT GGT GAT GCG AAG AGT GTT AAT GGC ATT GCT AAG GGA                  1047
Gly Gly Asp Ala Lys Ser Val Asn Gly Ile Ala Lys Gly
            340                 345
```

(2) INFORMATION FOR SEQ ID NO: 2:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO: 2:

```
Lys Asn Asp His Asp Asn His Lys Gly Thr Val Lys Asn Ala Val
 1               5                  10                  15

Asp Met Ala Lys Ala Ala Glu Glu Ala Ala Ser Ala Ala Ser Ala Ala
                20                  25                  30

Thr Gly Asn Ala Ala Ile Gly Asp Val Val Lys Asn Ser Gly Ala Ala
                35                  40                  45

Ala Lys Gly Gly Glu Ala Ala Ser Val Asn Gly Ile Ala Lys Gly Ile
     50                  55                  60

Lys Gly Ile Val Asp Ala Ala Gly Lys Ala Asp Ala Lys Glu Gly Lys
 65                  70                  75                  80

Leu Asp Ala Thr Gly Ala Glu Gly Thr Thr Asn Val Asn Ala Gly Lys
                85                  90                  95

Leu Phe Val Lys Arg Ala Ala Asp Asp Gly Gly Asp Ala Asp Asp Ala
                100                 105                 110

Gly Lys Ala Ala Ala Ala Val Ala Ala Ser Ala Ala Thr Gly Asn Ala
                115                 120                 125

Ala Ile Gly Asp Val Val Asn Gly Asp Val Ala Lys Ala Lys Gly Gly
    130                 135                 140

Asp Ala Ala Ser Val Asn Gly Ile Ala Lys Gly Ile Lys Gly Ile Val
145                 150                 155                 160

Asp Ala Ala Glu Lys Ala Asp Ala Lys Glu Gly Lys Leu Asn Ala Ala
                165                 170                 175

Gly Ala Glu Gly Thr Thr Asn Ala Asp Ala Gly Lys Leu Phe Val Lys
                180                 185                 190

Asn Ala Gly Asn Val Gly Gly Glu Ala Gly Asp Ala Gly Lys Ala Ala
                195                 200                 205

Ala Ala Val Ala Ala Val Ser Gly Glu Gln Ile Leu Lys Ala Ile Val
                210                 215                 220

His Ala Ala Lys Asp Gly Gly Glu Lys Gln Gly Lys Lys Ala Ala Asp
225                 230                 235                 240

Arg Thr Asn Pro Ile Asp Ala Ala Ile Gly Gly Ala Gly Asp Asn Asp
                245                 250                 255

Ala Ala Ala Ala Phe Ala Thr Met Lys Lys Asp Asp Gln Ile Ala Ala
                260                 265                 270

Ala Met Val Leu Arg Gly Met Ala Lys Asp Gly Gln Phe Ala Leu Lys
                275                 280                 285

Asp Ala Ala Ala His Glu Gly Thr Val Lys Asn Ala Val Asp Ile
                290                 295                 300

Ile Lys Ala Ala Ala Glu Ala Ala Ser Ala Ala Ser Ala Ala Thr Gly
305                 310                 315                 320

Ser Ala Ala Ile Gly Asp Val Val Asn Gly Asn Gly Ala Thr Ala Lys
                325                 330                 335

Gly Gly Asp Ala Lys Ser Val Asn Gly Ile Ala Lys Gly
                340                 345
```

(2) INFORMATION FOR SEQ ID NO: 3:

(i) SEQUENCE CHARACTERISTICS:
        (A) LENGTH: 283 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 3:

```
GCCGCTGGAT GGTGGTGAGA AGCAGGGTAA GAAGGCTGCG GATCGTACAA ATCCCATTGA      60
CGCGGCTATT GGGGGTGCGG GTGATAATGA TGCTGCTGCG GCGTTTGCTA CTATGAAGAA     120
GGATGATCAG ATTGCTGCTG CTATGGTTCT GAGGGGAATG GCTAAGGATG GGCAATTTGC     180
TTTGAAGGAT GCTGCTGCTG CTCATGAAGG GACTGTTAAG AATGCTGTTG ATATAATAAA     240
GGCTGCTGCG GAAGCTGCAA GTGCTGCAAG TGCTGCTACT GGT                       283
```

(2) INFORMATION FOR SEQ ID NO: 4:

(i) SEQUENCE CHARACTERISTICS:
        (A) LENGTH: 233 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 4:

```
TTTATTATAT CAACAGATTC TTAACAGTCC CTTCATGAGC AGCAGCAGCA TCCTTCAAAG      60
CAAATTGCCC ATCCTTAGCC ATTCCCCTCA GAACCATAGC AGCAGCAATC TGATCATCCT     120
TCTTCATAGT AGCAAACGCC GCAGCAGCAT CATTATCACC CGCACCCCCA ATAGCCGCGT     180
CAATCGGATT TGTACGATCC GCAGCCTTCT TACCCTGCTT CTCACCACCA TCC            233
```

(2) INFORMATION FOR SEQ ID NO: 5:

(i) SEQUENCE CHARACTERISTICS:
        (A) LENGTH: 194 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 5:

```
CCGTGCAAGC TGGGTTGAAG AAGGTTGGGG ATGTTGTTAA GAATAGTGAG GCAAAAGATG      60
GTGATGCGGC GAGTGTTAAT GGGATTGCTA AGGGGATAAA GGGGATTGTT GATGCTGCTG     120
AGAAGGCTGA TGCGAAGGAA GGGAAGTTGG TATGTGGCTG GTGCTGCTGG TGAAACTAAC     180
AAGGAAGCGG CCGC                                                       194
```

(2) INFORMATION FOR SEQ ID NO: 6:

(i) SEQUENCE CHARACTERISTICS:
        (A) LENGTH: 369 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 6:

```
GCGGCCGCTT GAGGAAGCTG CAAGTGCTGC AAGTGCTGCT ACTGGTAATG CAGCGATTGG      60
GGATGTTGTT AAGAATAGTG GGGCAGCAGC AAAAGGTGG GAGGCGGCGA GTGTTAATGG     120
GATTGCTAAG GGGATAAAGG GGATTGTTGA TGCTGCTGGA AAGGCTGATG CGAAGGAAGG     180
GAAGTTGGAT GCTACTGGTG CTGAGGGTAC GACTAACGTG AATGCTGGGA AGTTGTTTGT     240
GAAGAGGGCG GCTGATGATG GTGGTGATGC AGATGATGCT GGGAAGGCTG CTGCTGCGGT     300
```

```
TGCTGCAAGT GCTGCTACTG GTAATGCAGC GATTGGAGAT GTTGTTAATG GTGATGTGGC      360

AAAACAAAA                                                              369
```

(2) INFORMATION FOR SEQ ID NO: 7:

(i) SEQUENCE CHARACTERISTICS:
        (A) LENGTH: 142 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 7:

```
AAGGATGGTG ATGATAAGCA GGGTAAGAAG GCTGAGGATG CTACAAATCC GATTGACGCG      60

GCTATTGGGG GTGCAGGTGC GGGTGCTAAT GCTGCTGCGG CGTTTAATAA TATGAAGAAG      120

GATGATCAGA TTGAGCGGCC GC                                                142
```

(2) INFORMATION FOR SEQ ID NO: 8:

(i) SEQUENCE CHARACTERISTICS:
        (A) LENGTH: 210 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 8:

```
GGTGAAACTA ACAAGGATGC TGGGAAGTTG TTTGTGAAGA AGAATGGTGA TGATGGTGGT      60

GATGCAGGTG ATGCTGGGAA GGCTGCTGCT GCGGTTGCTG CTGTTAGTGG GGAGCAGATA      120

TTAAAAGCGA TTGTTGATGC TGCTAAAGAT GGTGATAAGA CGGGGGTTAC TGATGTAAAG      180

GATGCTACAA ATCCGATTGA CGCGGCTATT                                        210
```

(2) INFORMATION FOR SEQ ID NO: 9:

(i) SEQUENCE CHARACTERISTICS:
        (A) LENGTH: 236 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 9:

```
TATATAATAA AGGCTGCTGC GAAGCTGCAA GTGCTGCAAG TGCTGCTACT GGTAGTGCAG      60

CAATTGGGGA TGTTGTTAAT GGTAATGGAG CAACAGCAAA AGGTGGTGAT GCGAAGTGTT      120

AATGGGATTG CTAAGGGGAT AAAGGGGATT GTTGATGCTG CTGAGAAGGC TGATGCGAAG      180

GAAGGGAAGT TGGATGTGGC TGGTGATGCT GGTGAAACTA ACAAGGAAGC GGCCGC          236
```

(2) INFORMATION FOR SEQ ID NO: 10:

(i) SEQUENCE CHARACTERISTICS:
        (A) LENGTH: 199 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 10:

```
ATGAGAGGAT CTCATCACCA TCACCATCAC ACGGATCCCC CGGGCTGCAG GAATTCGCGG      60
```

```
CCGCTGAAGG CTGATGCGAA GGAAGGGAAG TTGGATGTGG CTGGTGCTGC TGGTGAAACT        120

AACAAGGATG CTGGGAAGTT GTTTGTGAAG AAGAATAATG AGGGTGGTGA AGCAAATGAT        180

GCTGGGAAGG CTGCTGCTG                                                    199
```

(2) INFORMATION FOR SEQ ID NO: 11:

(i) SEQUENCE CHARACTERISTICS:
        (A) LENGTH: 272 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 11:

```
GCCGCTGGAT GATCAGATTG CTGCTGCTAT GGTTGTGAGG GGAATGGCTA AGGATGGGCA         60

GTTTGCTTTG AAGGATGATG CTGCTAAGGA TGGAGATAAA ACGGGGGTTG CTGCGGATGT        120

GAAAATCCGA TTGACGCGGC TATTGGGGGT GCGGATGCTG ATGCTGCGGC GTTTAATAAG        180

GAGGGGATGA AGAAGGATGA TCAGATTGCT GCTGCTATGG TTCTGAGGGG AATGGCTAAG        240

GATGGGCAGT TTGCTTTGAC GAATAATGCT GC                                     272
```

(2) INFORMATION FOR SEQ ID NO: 12:

(i) SEQUENCE CHARACTERISTICS:
        (A) LENGTH: 289 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO: 12:

```
ACTGTTAAGA ATGCTGTTGA TATAATAAAG CTGCTGCGG AAGCTGCAAG TGCTGCAAGT          60

GCTGCTACTG GTAGTGCAGC AATTGGGGAT GTTGTTAATG GTAATGGAGC AACAGCAAAA       120

GGTGGTGATG CGAAGAGTGT TAATGGGATT GCTAAGGGGA TAAAGGGGAT TGTTGATGCT       180

GCTGAGAAGG CTGATGCGAA GGAAGGGAAG TTGGATGTGG CTGGTGATGC TGGTGAAACT       240

AACAAGGATG CTGGGAAGTT GTTTGTGAAG AACAATGGTA ATGAGGGTA                   289
```

(2) INFORMATION FOR SEQ ID NO: 13:

(i) SEQUENCE CHARACTERISTICS:
        (A) LENGTH: 142 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 2..142

(ix) FEATURE:
        (A) NAME/KEY: mat_peptide
        (B) LOCATION: 2

(xi) SEQUENCE DESCRIPTION: SEQ ID NO: 13:

```
G CCG CTT ACA AAT CCG ATT GAC GCG GCT ATT GGG GGG AGT GCG GAT            46
  Pro Leu Thr Asn Pro Ile Asp Ala Ala Ile Gly Gly Ser Ala Asp
   1               5                  10                  15

CGT AAT GCT GAG GCG TTT GAT AAG ATG AAG AAG GAT GAT CAG ATT GCT         94
```

```
                                                              -continued

Arg Asn Ala Glu Ala Phe Asp Lys Met Lys Lys Asp Gln Ile Ala
            20                  25                  30

GCT GCT ATG GTT CTG AGG GGA ATG GCT AAG GAT GGG CAG TTT GCT TTG          142
Ala Ala Met Val Leu Arg Gly Met Ala Lys Asp Gly Gln Phe Ala Leu
            35                  40                  45

(2) INFORMATION FOR SEQ ID NO: 14:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO: 14:

Pro Leu Thr Asn Pro Ile Asp Ala Ala Ile Gly Gly Ser Ala Asp Arg
 1               5                  10                  15

Asn Ala Glu Ala Phe Asp Lys Met Lys Lys Asp Gln Ile Ala Ala
            20                  25                  30

Ala Met Val Leu Arg Gly Met Ala Lys Asp Gly Gln Phe Ala Leu
            35                  40                  45
```